(12) United States Patent
Bauer

(10) Patent No.: US 9,453,810 B2
(45) Date of Patent: Sep. 27, 2016

(54) DEVICES AND METHODS FOR IDENTIFYING A BIOLOGICAL OR CHEMICAL RESIDUE IN AN AQUEOUS SAMPLE

(71) Applicant: Alan Joseph Bauer, Jerusalem (IL)

(72) Inventor: Alan Joseph Bauer, Jerusalem (IL)

( * ) Notice: Subject to any disclaimer, the term of this patent is extended or adjusted under 35 U.S.C. 154(b) by 314 days.

(21) Appl. No.: 13/975,340

(22) Filed: Aug. 25, 2013

(65) Prior Publication Data
US 2015/0053577 A1   Feb. 26, 2015

(51) Int. Cl.
*G01N 27/07* (2006.01)
*G01N 27/08* (2006.01)

(52) U.S. Cl.
CPC ............. *G01N 27/07* (2013.01); *G01N 27/08* (2013.01)

(58) Field of Classification Search
CPC .... G01N 33/04; G01N 27/327; G01N 27/74; G01N 15/0618; C12Q 1/02
See application file for complete search history.

(56) References Cited

U.S. PATENT DOCUMENTS

| | | | | |
|---|---|---|---|---|
| 3,403,081 A | * | 9/1968 | Rohrback | C12Q 1/001 204/403.01 |
| 4,246,343 A | * | 1/1981 | Wilkins | C12Q 1/04 204/403.01 |
| 5,269,174 A | * | 12/1993 | Chiba | G01N 11/00 73/54.01 |
| 5,583,432 A | * | 12/1996 | Barnes | G01N 33/49 324/204 |
| 6,227,040 B1 | * | 5/2001 | Hastings | G01N 29/032 73/54.41 |
| 2002/0070107 A1 | * | 6/2002 | Usinowicz | C02F 1/008 204/228.3 |
| 2010/0210022 A1 | * | 8/2010 | Madura | C12Q 1/37 436/86 |
| 2014/0327553 A1 | * | 11/2014 | Whitaker | G01D 4/002 340/870.02 |

FOREIGN PATENT DOCUMENTS

WO    WO03097861 A1  *  11/2003

OTHER PUBLICATIONS

Carley (Pediatr Nurs. 2003;29(3)).*

* cited by examiner

*Primary Examiner* — Jennifer Dieterle

(57) ABSTRACT

The invention discloses methods and devices for rapidly detecting a biological or other residue in a liquid sample. In some embodiments of the instant invention, a single electrode is employed to contact a flowing aqueous solution, with electrical outputs being recorded by an electrical metering device. Injection or flow of sample leads to changes in solution electrostatic behavior; those changes are recorded in the metering device, with absence of predetermined residues or targets yielding the highest signals. General and specific target detection may be performed with various embodiments of the instant invention.

9 Claims, 18 Drawing Sheets

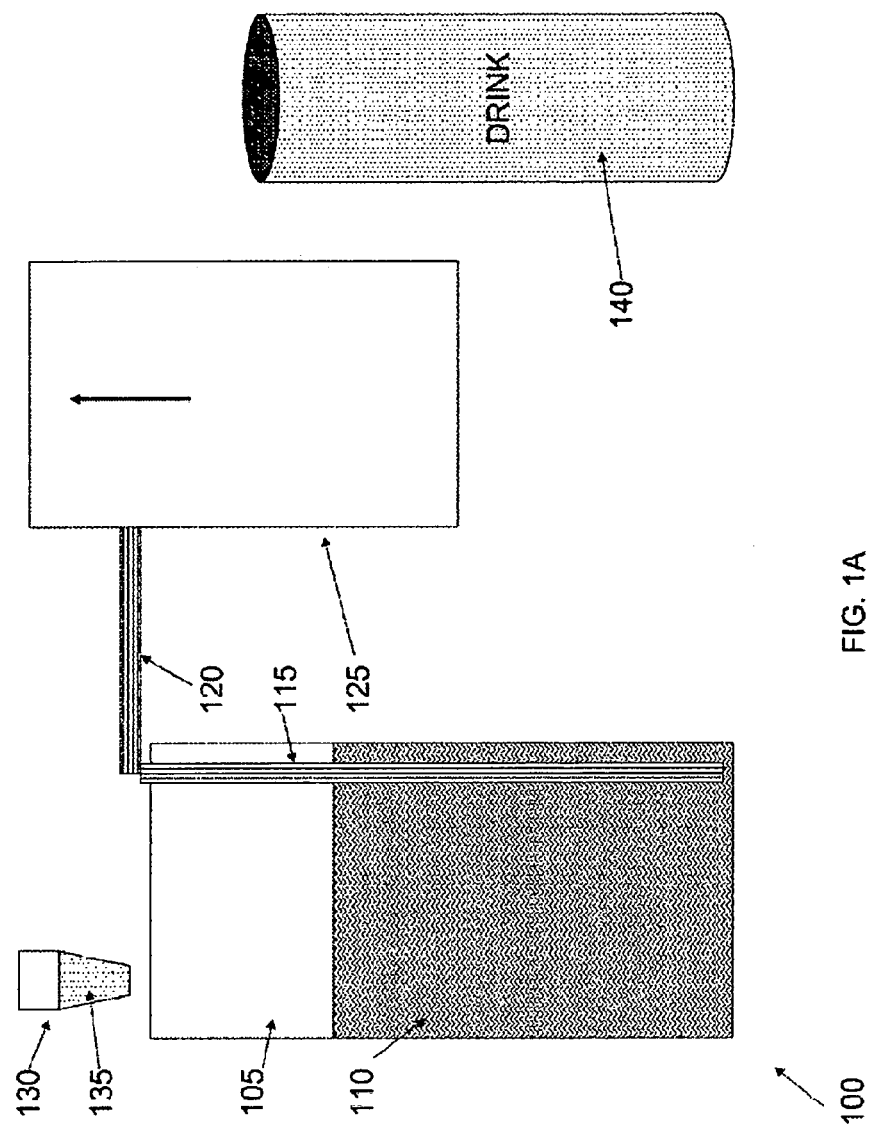

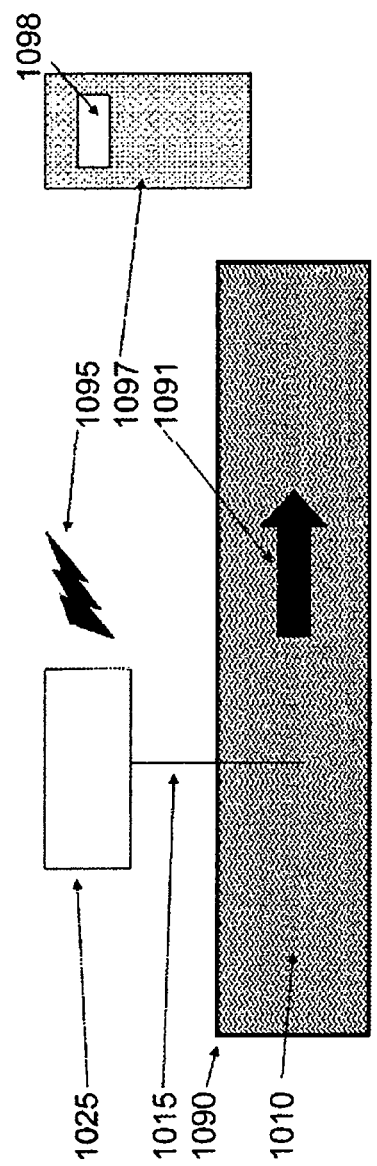
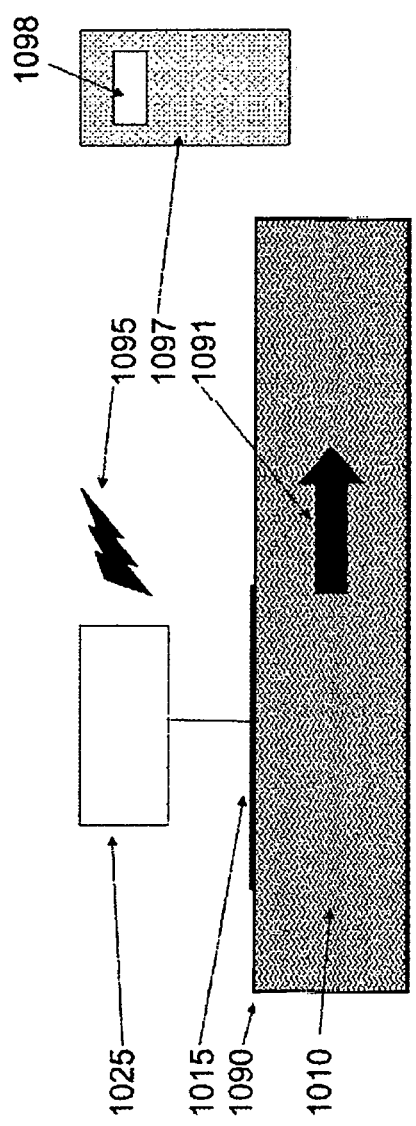
FIG. 10A
FIG. 10B

DEVICES AND METHODS FOR IDENTIFYING A BIOLOGICAL OR CHEMICAL RESIDUE IN AN AQUEOUS SAMPLE

The instant application claims benefit from the priority of U.S. Provisional Patent Application 61/842,979 filed 4 Jul. 2013 of identical inventorship.

FIELD AND BACKGROUND OF THE INVENTION

Chemical and biological sensors are devices that can detect or quantify analytes by virtue of interactions between targeted analytes and macromolecular binding agents such as enzymes, receptors, DNA strands, heavy metal chelators, or antibodies. Such sensors have practical applications in many areas of human endeavor. For example, biological and chemical sensors have potential utility in fields as diverse as blood glucose monitoring for diabetics, detection of pathogens commonly associated with spoiled or contaminated food, genetic screening, and environmental testing.

Chemical and biological sensors are commonly categorized according to two features, namely, the type of material utilized as binding agent and the means for detecting an interaction between binding agent and targeted analyte or analytes. Major classes of biosensors include enzyme (or catalytic) biosensors, immunosensors and DNA biosensors. Chemical sensors make use of synthetic macromolecules for detection of target analytes. Some common methods of detection are based on electron transfer, generation of chromophores, or fluorophores, changes in optical or acoustical properties, or alterations in electric properties when an electrical signal is applied to the sensing system.

Enzyme (or catalytic) biosensors utilize one or more enzyme types as the macromolecular binding agents and take advantage of the complementary shape of the selected enzyme and the targeted analyte. Enzymes are proteins that perform most of the catalytic work in biological systems and are known for highly specific catalysis. The shape and reactivity of a given enzyme limit its catalytic activity to a very small number of possible substrates. Enzymes are also known for speed, working at rates as high as 10,000 conversions per second per enzyme molecule. Enzyme biosensors rely on the specific chemical changes related to the enzyme/analyte interaction as the means for determining the presence of the targeted analyte. For example, upon interaction with an analyte, an enzyme may generate electrons, a colored chromophore or a change in pH (due to release of protons) as the result of the relevant catalytic enzymatic reaction. Alternatively, upon interaction with an analyte, an enzyme may cause a change in a fluorescent or chemiluminescent signal that can be recorded by an appropriate detection system.

Immunosensors utilize antibodies as binding agents. Antibodies are protein molecules that bind with specific foreign entities, called antigens, which can be associated with disease states. Antibodies attach to antigens and may remove the antigens from a host. Additionally or alternatively, the antibodies may trigger an immune response. Antibodies are quite specific in their interactions and, unlike enzymes, they are capable of recognizing and selectively binding to very large bodies such as single cells. Thus, antibody-based biosensors allow for the identification of certain pathogens such as dangerous bacterial strains. As antibodies generally do not perform catalytic reactions, there is a need for special methods to record the moment of interaction between target analyte and recognition agent antibody. Changes in mass (surface plasmon resonance, acoustic sensing) are often recorded; other systems rely on fluorescent probes that give signals responsive to interaction between antibody and antigen. Alternatively, an enzyme bound to an antibody can be used to deliver the signal through the generation of color or electrons; the enzyme-linked immunosorbent assay (ELISA) is based on such a methodology.

DNA biosensors utilize the complementary nature of the nucleic acid double-strands and are designed for the detection of DNA or RNA sequences usually associated with certain bacteria, viruses or given medical conditions. A sensor generally uses single-strands from a DNA double helix as the binding agent. The nucleic acid material in a given test sample is then denatured and exposed to the binding agent. If the strands in the test sample are complementary to the strands used as binding agent, the two interact. The interaction can be monitored by various means such as a change in mass at the sensor surface or the presence of a fluorescent or radioactive signal. Alternative arrangements provide binding of the sample of interest to the sensor and subsequent treatment with labeled nucleic acid probes to allow for identification of the sequences of interest.

Chemical sensors make use of non-biological macromolecules as binding agents. The binding agents show specificity to targeted analytes by virtue of the appropriate chemical functionalities in the macromolecules themselves. Typical applications include gas monitoring or heavy metal detection; the binding of analyte may change the conductivity of the sensor surface or lead to changes in charge that can be recorded by an appropriate field-effect transistor (FET). Several synthetic macromolecules have been used successfully for the selective chelation of heavy metals such as lead.

Known methods of detecting interaction of analyte and binding agent can be grouped into several general categories: chemical, optical, acoustical, and electrical. In the last, a voltage or current is applied to the sensor surface or an associated medium. As binding events occur on the sensor surface, there are changes in electrical properties of the system. The leaving signal is altered as function of analyte presence.

The most relevant prior art to the present invention involves sensors that are based on electrical means for analyte detection. There are several classes of sensors that make use of applied electrical signals for determination of analyte presence. Amperometric sensors make use of oxidation-reduction chemistries in which electrons or electrochemically active species are generated or transferred due to analyte presence. An enzyme that interacts with an analyte may produce electrons that are delivered to an appropriate electrode; alternatively, an amperometric sensor may employ two or more enzyme species, one interacting with analyte, while the other generates electrons as a function of the action of the first enzyme, an arrangement known as a coupled enzyme system. Glucose oxidase has been used frequently in amperometric biosensors for glucose quantification for diabetics. Other amperometric sensors make use of electrochemically active species whose presence alters the system applied voltage as recorded at a given sensor electrode. Not all sensing systems can be adapted for electron generation or transfer, and thus many sensing needs cannot be met by amperometric methods alone. The general amperometric method makes use of an applied voltage and effects of electrochemically active species on said voltage. An example of an amperometric sensor is described in U.S.

Pat. No. 5,593,852 to Heller, et al., which discloses a glucose sensor that relies on electron transfer effected by a redox enzyme and electrochemically-active enzyme cofactor species.

An additional class of electrical sensing systems includes those sensors that make use primarily of changes in an electrical response of the sensor as a function of analyte presence. Some systems pass an electric current through a given medium. If analyte is present, there is a corresponding change in an exit electrical signal, and this change implies that analyte is present. In some cases, the binding agent-analyte complex causes an altered signal, while in other systems, the bound analyte itself is the source of changed electrical response. Such sensors are distinguished from amperometric devices in that they do not necessarily require the transfer of electrons to an active electrode. Sensors based on the application of an electrical signal are not universal, in that they depend on alteration of voltage or current as a function of analyte presence; not all sensing systems can meet such a requirement. An example of this class of sensors is U.S. Pat. No. 5,698,089 to Lewis, et al., which discloses a chemical sensor in which analyte detection is determined by a change of an applied electrical signal. Binding of analyte to chemical moieties arranged in an array alters the conductivity of the array points; unique analytes can be determined by the overall changes in conductivity of all of the array points. The present invention does not rely on arrays or changes of applied electrical signal as a function of analyte presence. The present sensor does not require any applied electrical or electromagnetic signal.

Several other publications that do not fall into the preceding categories are worthy of mention in the prior art. The document, *Direct Observation of Enzyme Activity with the Atomic Force Microscope*. Radmacher, Manfred et al. Science 265:1577, 9 Sep. 1994 noted the existence of augmented spatial fluctuations in enzymes interacting with substrates, but did not apply this phenomenon to analyte detection.

U.S. Pat. No. 5,620,854 to Holzrichter, et al., proposed the use of macromolecule motion to detect analyte. The disclosed system relies specifically on atomic force or scanning tunneling microscopes for detection of said motion.

U.S. Pat. No. 5,114,674 to Stanbro, et al. discloses a sensor that is based on the interference of applied electrical fields. Interaction of target analyte with a binding agent alters the interference of the applied electrical field.

Other prior-art voltage-based sensors require the use of semiconducting field-effect transistors and rely on the chemical generation or physical trapping of charged species near the sensor surface. This approach has found widespread use in the detection of positively-charged heavy metals as well as analytes that are involved in proton (H+) generating enzyme reactions. The document *Endoscopic Urease Sensor System for Detecting Helicobacter pylori on Gastric Mucosa*, Sato et al. Gastrointestinal Endoscopy 49:32-38 (1999) describes a pH-sensitive FET for the detection of the enzyme urease, associated with the pathogenic bacterium *H. pylori*.

While hundreds of sensors have been described in patents and in the scientific literature, actual commercial use of such sensors remains limited. In particular, virtually all sensor designs set forth in the prior art contain one or more inherent weaknesses. Some lack the sensitivity and/or speed of detection necessary to accomplish certain tasks. Other sensors lack long-term stability. Still others cannot be sufficiently miniaturized to be commercially viable or are prohibitively expensive to produce. Some sensors must be pre-treated with salts and/or enzyme cofactors, a practice that is inefficient and bothersome. To date, virtually all sensors are limited by the known methods of determining that contact has occurred between an immobilized binding agent and targeted analytes. Use of fluorescent or other external detection probes adds to sensor production requirements and reduces lifetimes of such sensor systems. Additionally, the inventor believes that there is no sensor method disclosed in the prior art that is generally applicable to the vast majority of macromolecular binding agents, including enzymes, antibodies, antigens, nucleic acids, receptors, and synthetic binding agents.

SUMMARY OF THE INVENTION

It is therefore a purpose of the present invention, in some embodiments, to provide methods and devices for detecting the presence of at least one predetermined residue in an aqueous sample through the action of flowing a portion of said sample past a single electrode associated with an electrical metering device.

The invention includes a device for identifying the presence of a biological residue in a liquid sample, including: a container adapted to hold a liquid material; an aqueous solution disposed in a portion of the container; an electrically conductive element disposed partially in the solution in the container; an electrical meter adapted to be in electrical communication with a dry region of the conductive element through the agency of a single electrical contact; and, a liquid delivery element adapted to inject a portion of the sample into the aqueous solution disposed in the container.

In one aspect of the device, the container is realized as a plurality of disposable containers.

In another aspect of the device, the electrical meter is realized as a voltmeter component of a multifunctional detection device.

In another aspect of the device, the detection device is realized as a mobile computing device.

In another aspect of the device, the liquid sample is realized as a potable liquid.

In another aspect of the device, the liquid delivery element is realized as a pipette, micro-pipette, syringe, hose or microfluidic system.

In another aspect of the device, the conductive element is realized as aluminum foil or a conductive coating on an inner side of a portion of the container.

In another aspect of the device, the electrical meter is electrically insulated from its surroundings.

The invention also includes a device for identifying the presence of a predetermined chemical or biological residue in an aqueous sample, including: a disposable container; an electrically conductive element disposed partially in the solution in the container; a voltmeter adapted to be in electrical contact with a dry region of the disposable container; a liquid delivery element adapted to inject a portion of the water sample into the aqueous solution disposed in the container; a computing device in electrical communication with the voltmeter; and, software for determining the presence of the bacterial residue as a function of a voltage output from the voltmeter.

In one aspect of the device, the computing device is realized as a smartphone.

In another aspect of the device, the device is under the control of at least one application associated with the smartphone.

In another aspect of the device, wherein the conductive element is coated with a plurality of binding agents showing some level of specificity of interaction with a predetermined analyte.

In another aspect of the device, the bacterial residue is from a fecal source.

In another aspect of the device, the voltage output varies inversely with the presence of the chemical or biological residue.

The invention includes a method for determining the presence of a biological residue in a liquid sample, including the following: providing a sample; providing a disposable container adapted to hold a liquid material; placing a conductive element in a portion of the container; adding an aqueous solution to a predetermined volume within the container, wherein a portion of the conductive element is in physical contact with the aqueous solution; attaching a dry region of the conductive element to an electrical metering device, wherein the contact involves a single electrical connection between the conductive element and the device; injecting a portion of the liquid sample into the aqueous solution; measuring a change in an electrical parameter in the aqueous solution with the electrical metering device; and, determining the presence of the biological residue in the liquid sample as a function of a value of the change in the electrical parameter.

In one aspect of the method, the liquid sample is realized as a drink amenable to human consumption.

In another aspect of the method, the disposable container is made of plastic or polymeric material.

In another aspect of the method, the conductive element is physically associated with the container.

In another aspect of the method, the determining is performed by associating a lower value for the electrical parameter for presence of the biological residue.

In another aspect of the method, the electrical parameter is AC or DC voltage.

The invention provides for a method for detecting the presence of a residue in a liquid sample, including the following: providing a plastic element; placing the plastic element in the sample, and optionally drawing a portion of the sample into the plastic element; approaching the plastic element towards a conductive element in electrical communication with an electrical metering device; and, determining presence of the residue by the electrical output recorded by the electrical metering device.

In one aspect of the method, the residue is bacteria and the sample is water.

In another aspect of the method, the electrical metering device is realized as a voltmeter.

In another aspect of the method, the determining is performed by analyzing the output, the lower the output the more of the residue present.

In another aspect of the method, the approaching is realized as bringing the plastic element to within 10 centimeters of the conductive element.

The invention includes a method for determining the presence of a biological residue in a liquid sample, including the following: providing a sample; providing a container adapted to hold a liquid material; placing a conductive element in a portion of the container; adding an aqueous solution to a predetermined volume within the container, wherein a portion of the conductive element is in physical contact with the aqueous solution; attaching a dry region of the conductive element to an electrical metering device, wherein the contact involves a single electrical connection between the conductive element and a single terminal of the device; approaching the container with a liquid delivery element containing of a portion of the liquid sample; allowing readings in the electrical metering device to approach a zero value; injecting a portion of the liquid sample into the aqueous solution; measuring a change in an electrical parameter with the electrical metering device; and, determining the presence of the biological residue in the liquid sample as a function of a value of the change in the electrical parameter.

In one aspect of the method, the container is disposable.

In another aspect of the method, the electrical parameter is selected from AC voltage, DC voltage, and AC+DC voltage.

In another aspect of the method, the approaching involves bringing the liquid delivery device to within 10 centimeters of the container.

The invention also includes a method for determining the presence of a biological residue in a liquid sample, including the following: providing a sample; providing a container adapted to hold a liquid material; placing a conductive element in a portion of the container; attaching a region of the conductive element to an electrical metering device, wherein the contact involves a single electrical connection between the conductive element and a single terminal of the device; approaching the container with a liquid delivery element containing of a portion of the liquid sample; allowing readings in the electrical metering device to approach a zero value; injecting a portion of the liquid sample into the container; measuring a change in an electrical parameter with the electrical metering device; and, determining the presence of the biological residue in the liquid sample as a function of a value of the change in the electrical parameter.

In one aspect of the method, the conductive element is realized as aluminum foil or conductive paint.

The invention also provides for a method for determining the presence of a biological residue in a liquid sample, including the following: providing a sample; providing a conductive element; attaching a region of said conductive element to an electrical metering device, wherein said contact involves a single electrical connection between said conductive element and a single terminal of said device; approaching said conductive element with a liquid delivery element containing of a portion of said liquid sample; allowing readings in said electrical metering device to approach a zero value; injecting a portion of said liquid sample onto or in the vicinity of said conductive element; measuring a change in an electrical parameter with said electrical metering device; and, determining the presence of the biological residue in the liquid sample as a function of a value of the change in the electrical parameter.

In one aspect of the method, the vicinity is five centimeters or less.

The invention includes a device for identifying the presence of a biological or chemical residue in a liquid sample, including: a flowing liquid sample; an electrically conductive element disposed partially in proximity to the flowing liquid sample; an electrical meter adapted to be in electrical communication with a dry region of the conductive element through the agency of a single electrical terminal; and, a controller element adapted to receive readings from the meter and provide a signal to a user as to a presence of the residue in the liquid sample.

In one aspect of the device, the liquid sample is made to flow in a pipette, air, pipe, tube, faucet, sink, shower, toilet or liquid delivery element.

In another aspect of the device, the liquid is water.

In another aspect of the device, the electrical meter is realized as a meter adapted to read AC voltage, DC voltage, Hertz, electrical resistance or AC+DC voltage.

In another aspect of the device, the controller element is associated with one of the following: the electrical meter, a computing device, a handheld computing device, a smartphone or a mobile computing device.

In another aspect of the device, the electrically conductive element is in physical contact with the liquid.

In another aspect of the device, the electrically conductive element is in physical contact with the pipette, air, pipe, tube, faucet, sink, shower, toilet or liquid delivery element.

In another aspect of the device, the electrically conductive element is realized as a plurality of electrically conductive elements.

In another aspect of the device, the electrically conductive elements are coated with a plurality of binding agents adapted to interact with predetermined levels of specificity with one or a plurality of predetermined analytes.

The invention includes a method for determining the quality of a liquid sample, including the following: causing a portion of the liquid sample to flow in a predetermined direction; approaching a conductive element towards the flowing liquid sample, wherein the conductive element is adapted to be in electrical communication via a single electrical connection with an electrical metering device; recording electrical readings with the electrical metering device; comparing the electrical readings with predetermined electrical reading values associated with high quality and low quality samples of the liquid; and, determining the quality of the liquid as a function of electrical readings associated with the liquid as compared to the electrical reading values associated with the high quality and low quality samples of the liquid.

In aspect of the method, the step of approaching includes physically contacting the conductive element to the flowing water sample.

In another aspect of the method, the step of approaching includes contacting the conductive element to a pipette, air, pipe, tube, or other element in which the liquid is flowing.

In another aspect of the method, the recording is performed by a computing device.

In another aspect of the method, the determining involves comparing the electrical readings to predetermined electrical reading values associated with predetermined quality states of the liquid.

In another aspect of the method, the quality of the liquid system is determined by the electrical readings being above or below a predetermined value associated with the flowing liquid sample.

The invention additionally includes a device for identifying the presence of a predetermined chemical or biological residue in an aqueous sample, including: a disposable container; an electrically conductive element disposed partially in the solution in the container; a voltmeter adapted to be in electrical contact with a dry region of the disposable container; a liquid delivery element adapted to inject a portion of the water sample into the aqueous solution disposed in the container; a computing device in electrical communication with the voltmeter; and, software for determining the presence of the bacterial residue as a function of a voltage output from the voltmeter.

In one aspect of the device, the computing device is realized as a smartphone or mobile computing device.

In another aspect of the device, the device is under the control of at least one application associated with the smartphone.

In another aspect of the device, the conductive element is coated with a plurality of binding agents showing some level of specificity of interaction with a predetermined analyte.

In another aspect of the device, the voltage output varies inversely with the presence of the chemical or biological residue.

Unless otherwise defined, all technical and/or scientific terms used herein may have the same general meanings as commonly understood by a practitioner of ordinary skill in the art to which the invention pertains. An electrical meter or electrical metering device may include but not be limited to a voltmeter, ammeter, resistance meter, Hertz meter, CPS meter, oscilloscope, dielectric measurement unit or other device capable of receiving and/or processing an electrical signal or input. A disposable container may be any container of any material, wherein the container is adapted to be capable of holding a liquid sample. "Conductor" and "electrode" may have their generally understood meanings as known in the electrical arts. An "aqueous solution" may generally be any water-based solution that may possibly include salts or other materials. A "liquid delivery element" may generally refer to an element capable of discharging a liquid sample into or in the vicinity of a disposable container. Pipettes, microliter fluid dispensers, microfluidic systems, and syringes are non-limiting examples of liquid delivery elements. A "mobile computing device" may be a cellular phone, a smartphone, tablet computer, mobile computing device, laptop computer or other appropriate computing device. Aluminum foil for the instant invention may be coated or uncoated and may be used as supplied by manufacturer. "Residue" may generally refer to bacterial or chemical material present in and the subject of detection in an aqueous solution. Residues may include bacteria, viral particles, predetermined chemical or chemical classes, metals, small molecules, macromolecules, or other predetermined materials or groups of materials. "Binding agents" may generally refer to antibodies, nucleic acids, receptors or other molecules/macromolecules that may bind or interact with a predetermined analyte or group of analytes with some level of specificity of interaction. An analyte or target may generally be a material that is the subject of detection and/or quantification. Bacteria and viruses are non-limiting examples of potential targets for the instant invention. "Plastic element" may generally refer to any material made of plastic or polymer. A preferred plastic element is a polypropylene tip of a micro-pipette. A plastic element may allow for sample uptake and ejection or it may be without an internal volume for sample receipt. A "terminal" may have its generally understood meaning as it relates to an electrical metering device. A non-limiting example of a terminal is the Voltage-Resistance terminal/hole on a multimeter [not the COM terminal and not the current terminal]. An electrode is generally attached to a terminal of an electrical metering device and in the instant invention, there is generally no electrical circuit involving a conductive element—that is, the conductive element contacts a metering device at one point, without the element being part of an electric circuit.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. It is noted that similar elements in various drawings will have the same number, advanced by the appropriate multiple of 100.

In the drawings:

FIGS. 1A-1B show schematic views of an embodiment of the instant invention;

DESCRIPTION OF SPECIFIC EMBODIMENTS OF THE INVENTION

Figure 1B:
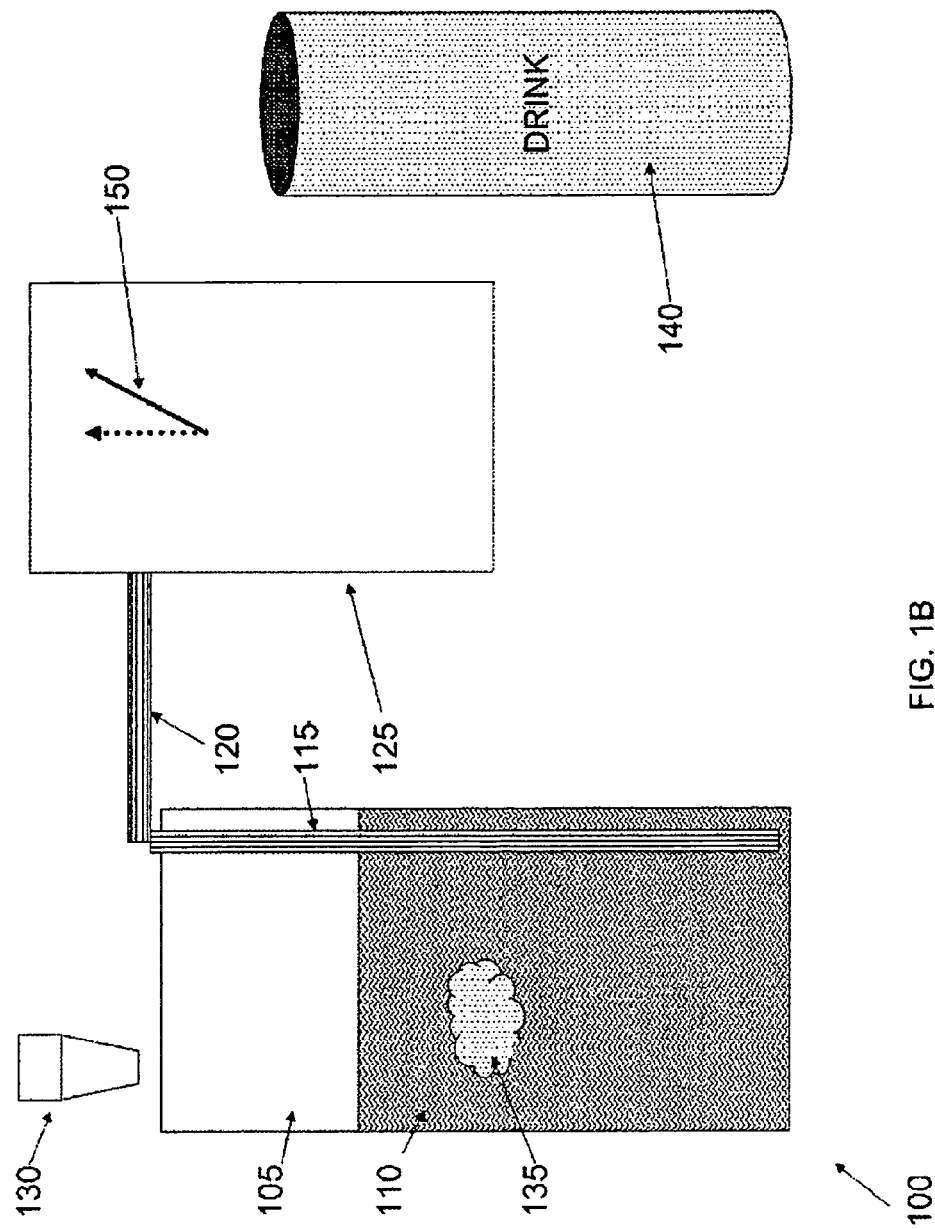

The present invention, in some embodiments thereof, relates to systems and devices for quickly and facilely detecting the presence of bacteria or other materials in aqueous samples. Without being bound by any particular theory, the following discussion is offered to facilitate understanding of the invention. The present invention, in some embodiments, provides for measuring voltage or other electrical signal from a single electrical lead as a function of addition of an aqueous sample of interest.

The instant invention, in some embodiments, provides for the rapid detection of bacterial or other biological residues in water or drinking liquids. The invention, in some embodiments, provides for an electrical metering device with a single electrode placed in or in close proximity to an aqueous solution. A predetermined volume of a sample is added to the solution, and immediately during and after addition of said sample to said solution, a change in an electrical property is recorded by said meter through the agency of said single electrode. No electrical signal is applied to the electrode or solution and there is no electrical circuit, as only one electrode is employed.

For purposes of better understanding, some embodiments of the present invention are illustrated in the figures of the drawings.

First Embodiment

Attention is turned to FIG. 1A which shows a schematic view of a device 100 according to the instant invention. A disposable container 105 includes an aqueous solution 110 in a portion of the container 105 volume. A conductive element 115 is partially submerged in said solution 110 and partially exposed above the solution 110. The conductive element 115 is attached through the agency of a single electrode 120 to a metering device 125 that is adapted to record and possibly display a predetermined electrical signal. The device 100 additionally includes a liquid delivery element 130 that includes a portion 135 of a sample 140 that is the subject of testing. FIG. 1A shows the device 100 immediately prior to additional of said portion 135 to said aqueous solution 110. It is understood that single electrode 120 could be placed in the solution 110, but doing so would dirty the electrode 120 with said portion 135 of sample; as such, the conductive element 115 is associated with or added to said container 105, while said electrode 120 is attached to said conductive element 115 during biosensing action. Contact of electrode 120 and conductive element 115 generally occurs in a clean and dry portion of conductive element 115.

Attention is turned to FIG. 1B which shows that the portion 135 formerly in the liquid delivery element 130 has been injected into solution 110. The conductive element 115 senses changes in the electrostatic fields in the solution 110 and said changes are recorded in the metering device 125 via the single electrode 120 connecting the metering device 125 and the conductive element 115. In general, clean sample 140 gives a relatively high electrical reading 150 in say AC or DC voltage. Presence of bacteria [not shown] or other residues tends to cause output readings in the metering device to decrease. To note, there is only one electrode in use in the instant embodiment of the present invention. There is no need for a counter electrode, second electrode, introduction of voltage or current into the system from an exogenous source or the like. It is also understood that the metering device 125 may be a component of a detection unit [not shown] and may have a plurality of functions including but not limited to measuring a change in an electric signal, display said change, providing an alert. The metering device 125 may be electrically isolated in a Rutherford Cage or the like, though such arrangements are not shown in the instant embodiment.

Second Embodiment

Figure 2:
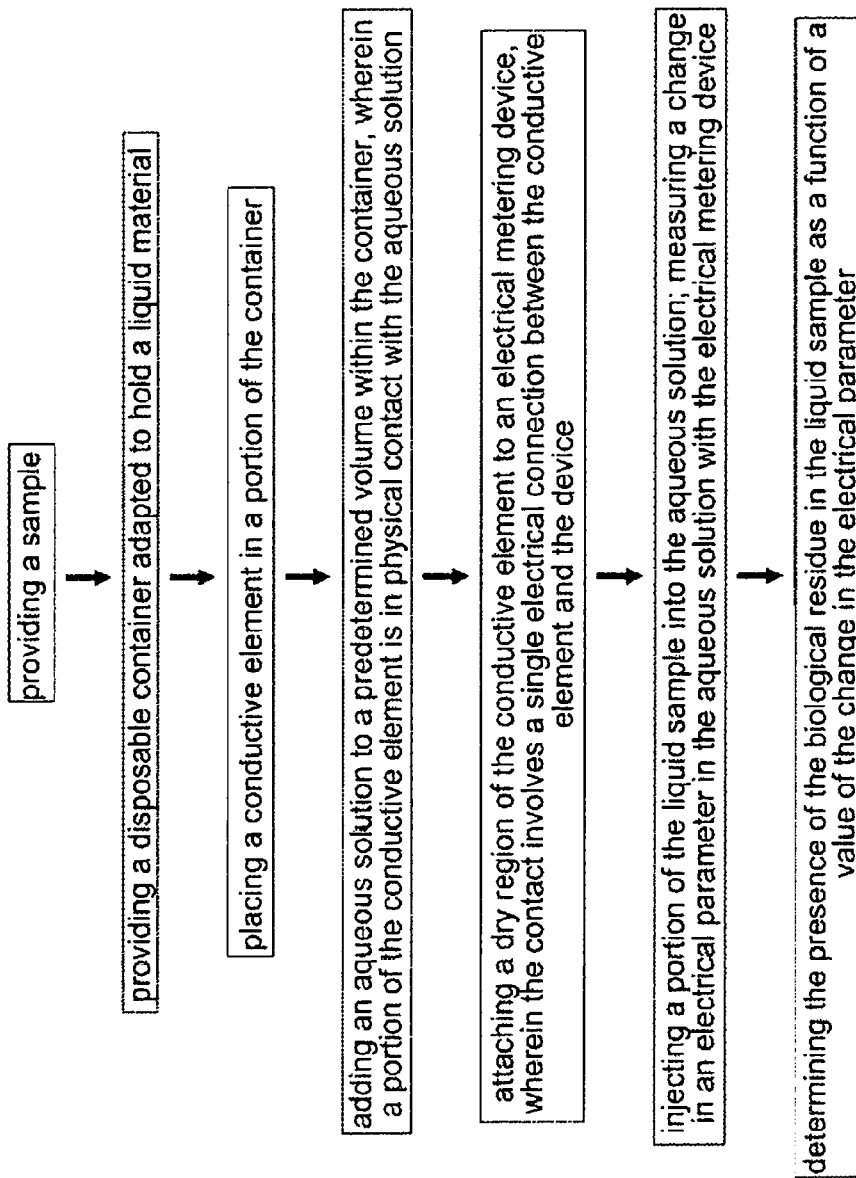
FIG. 2 shows a method associated with the instant invention.

Attention is turned to FIG. 2 which shows a method associated with the instant invention. The invention includes a method for determining the presence of a biological residue in a liquid sample, including the following: providing a sample; providing a disposable container adapted to hold a liquid material; placing a conductive element in a portion of the container; adding an aqueous solution to a predetermined volume within the container, wherein a portion of the conductive element is in physical contact with the aqueous solution; attaching a dry region of the conductive element to an electrical metering device, wherein the contact involves a single electrical connection between the conductive element and the device; injecting a portion of the liquid sample into the aqueous solution; measuring a change in an electrical parameter in the aqueous solution with the electrical metering device; and, determining the presence of the biological residue in the liquid sample as a function of a value of the change in the electrical parameter. Samples may be water or any water-based solution. Soft drinks, municipal water, mineral water, waste water, reclaimed water, desalinated water, beer, and other drinks are non-limiting examples of samples that may be tested according to the instant method embodiment. A portion or all of a sample may be injected into a container which may include an aqueous solution. The instant method works without said aqueous solution present but performance and discrimination appear improved with an aqueous solution in a portion of the container. The conductive element may be any conductive or semiconductive material. The conductive element may be a portion of the container, such as a conducting coating on an inner surface of the container. Alternatively, the conductive element may be an independent element added to the container any time prior to sample addition to container. The container may be a single container or a plurality of containers such as 96 wells of a 96 well plate. The container is generally made of a plastic or polymeric material. Said attaching may generally be performed by contacting an electrode, lead or the like associated with the electrical metering device to the conductive element. There is only one lead in the instant method and there is no electrical circuit according to the present invention. The electrode contacts the electrical element and thus provides electrical communication between the electrical element in the solution and the electrical metering device. In the absence of injection or addition of sample, there is either no signal or a background signal. Change in signal is measured during and immediately after addition of sample or a portion thereof. If voltage, either AC or DC, is measured, microvolts or millivolts are recorded, with a change in voltage being related to the absence or presence of a predetermined residue such as bacteria, viral particles, or other biological material.

Third Embodiment

Figure 3:
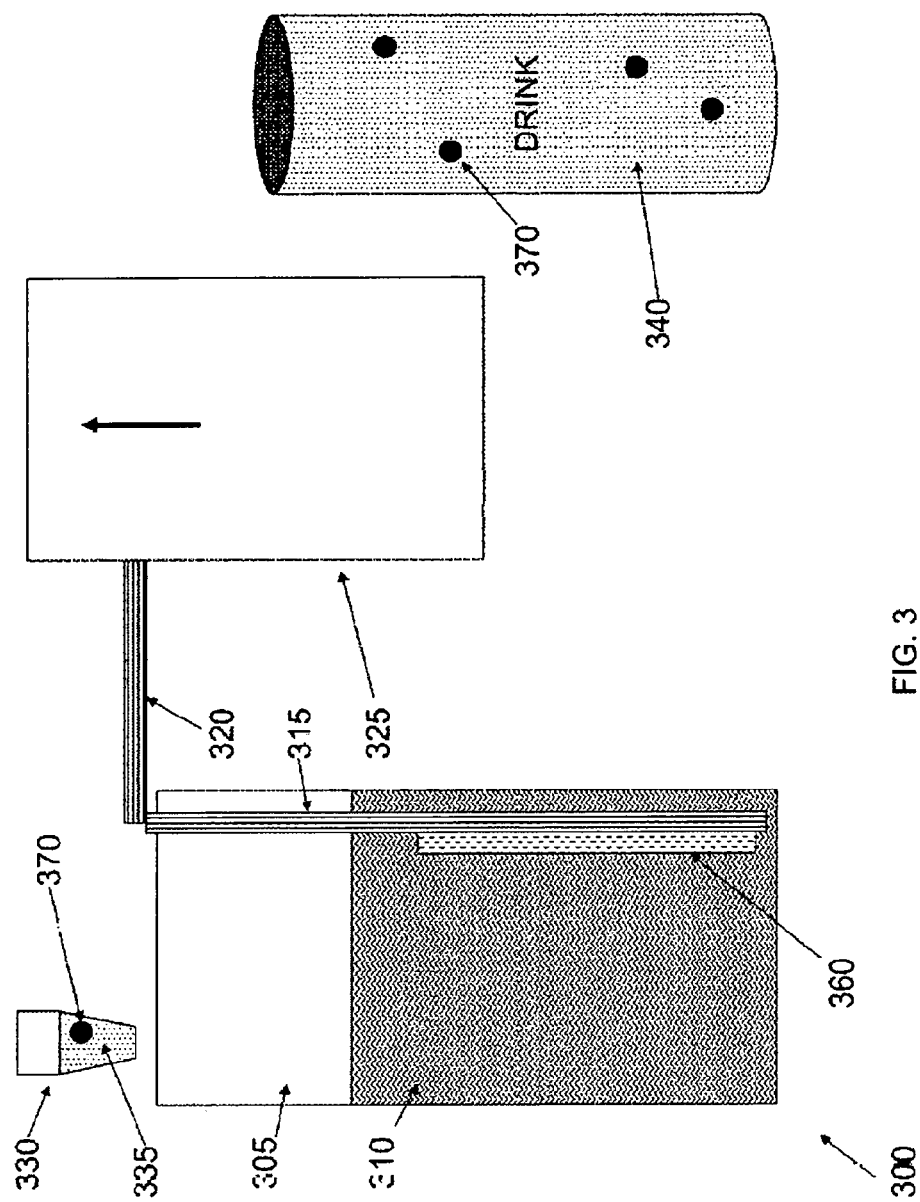
FIG. 3 shows a schematic view of an alternative embodiment of the instant invention.

Attention is turned to FIG. 3 which shows a schematic view of a device 300 according to the instant invention. A container 305 includes an aqueous solution 310 in a portion of the container 305 volume. A conductive element 315 coated with binding agents 360 such as antibodies against a predetermined target 370 is partially submerged in said solution 310 and partially exposed above the solution 310. The conductive element 315 is attached through the agency of a single electrode 320 to a metering device 325 that is adapted to record and possibly display a predetermined electrical signal. The device 300 additionally includes a liquid delivery element 330 that includes a portion 335 of a sample 340 that is the subject of testing. FIG. 3 shows the device 300 immediately prior to additional of said portion 335 that includes said target 370 to said aqueous solution 310. The binding agents 360 may be a single or multi-layer coating associated with the conductive element 315 and is shown as a single layer for convenience only. Presence of analyte 370 in sample 340 generally leads to depressed output readings as recorded in the metering device 325. It is believed that analyte associated cations in an electric double layer are the reasons for the reduced electrical signal seen in the metering device 325. The binding agents 360 may be coated on all or a part of the conductive element 315.

Fourth Embodiment

Figure 4:
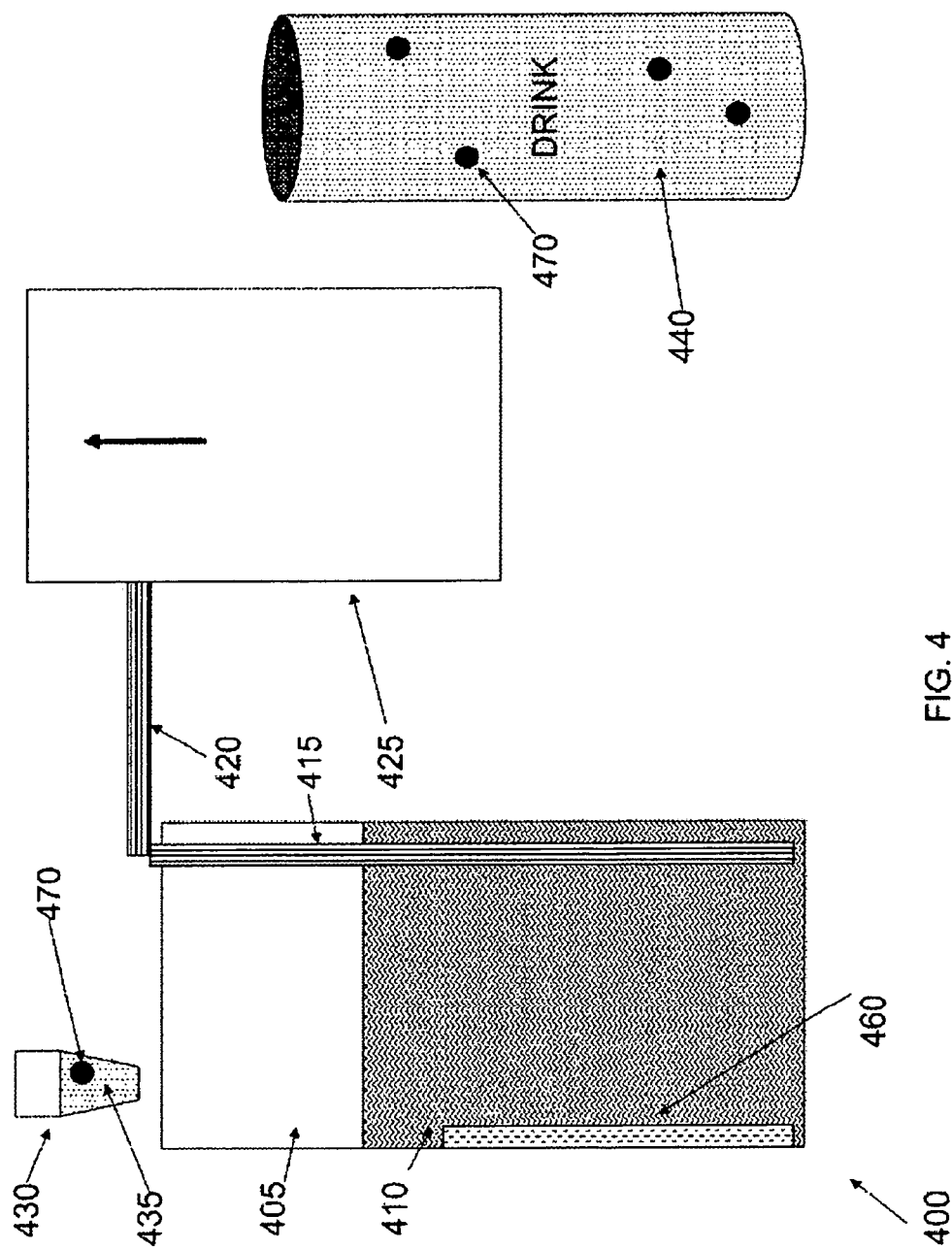
FIG. 4 shows a schematic view of an alternative embodiment of the instant invention.

Attention is turned to FIG. 4 which shows a schematic view of a device 400 according to the instant invention. A container 405 includes an aqueous solution 410 in a portion of the container 405 volume. A conductive element 415 is present partially in solution 410 and partially out of solution 410. Binding agents 460 such as antibodies against a predetermined target 470 are present and may be free in solution 410 or bound to a solid element in the container 405; in the instant figure, the binding agents 460 are shown bound to an inner side of said container 405. The conductive element 415 may be attached through the agency of a single electrode 420 to a metering device 425 that is adapted to record and possibly display a predetermined electrical signal. The device 400 additionally includes a liquid delivery element 430 that includes a portion 435 of a sample 440 that is the subject of testing. FIG. 4 shows the device 400 immediately prior to additional of said portion 435 that includes said target 470 to said aqueous solution 410. The binding agents 460 may be a single or multi-layer coating associated with the conductive element 415 and is shown as a single layer for convenience only. Presence of analyte 470 in sample 440 generally leads to depressed output readings as recorded in the metering device 425. It is believed that analyte associated cations in an electric double layer are the reasons for the reduced electrical signal seen in the metering device 425. The binding agents 460 may be coated on one or a plurality of solid elements such as magnetic beads [not shown]

Fifth Embodiment

Figure 5A:
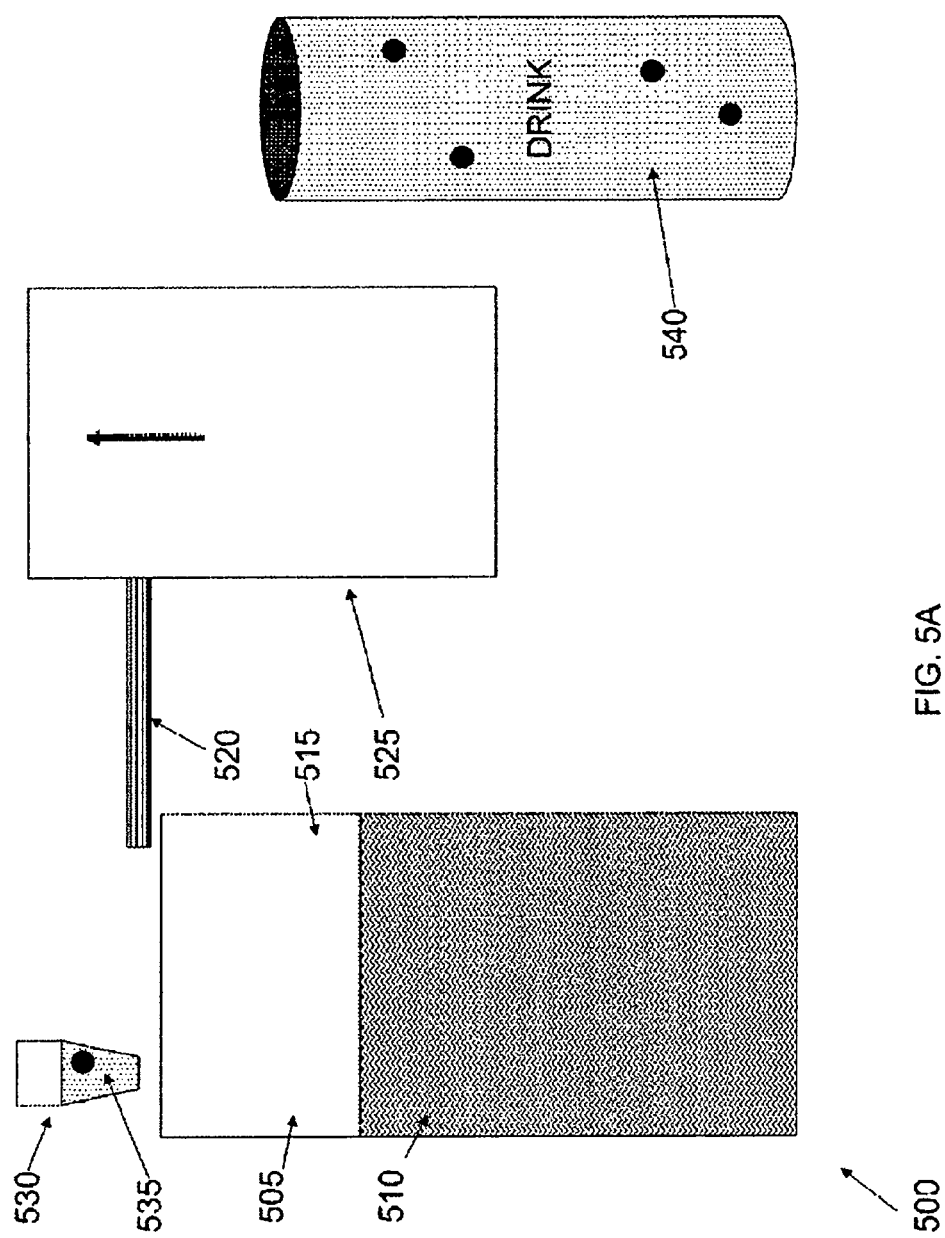
FIGS. 5A-5B show schematic views of an alternative embodiment of the instant invention.

Attention is turned to FIG. 5A which shows a schematic view of a device 500 according to the instant invention. A container 505 includes an aqueous solution 510 in a portion of the container 505 volume. A single electrode 520 of a metering device 525 that is adapted to record and possibly display a predetermined electrical signal such as voltage or current is placed either on or in near proximity to the container 505. Near proximity for the instant invention may generally refer to 0-10 centimeters from the container 505 to the electrode 520. The device 500 additionally includes a liquid delivery element 530 that includes a portion 535 of a sample 540 that is the subject of testing. FIG. 5 shows the device 500 immediately prior to additional of said portion 535 to said aqueous solution 510. It is understood that single electrode 520 could be placed in the solution 510, but doing so would dirty the electrode 520 with said portion 535 of sample; as such, the electrode 520 is placed either on or near the container 505, without any requirement for a conductive element.

Figure 5B:
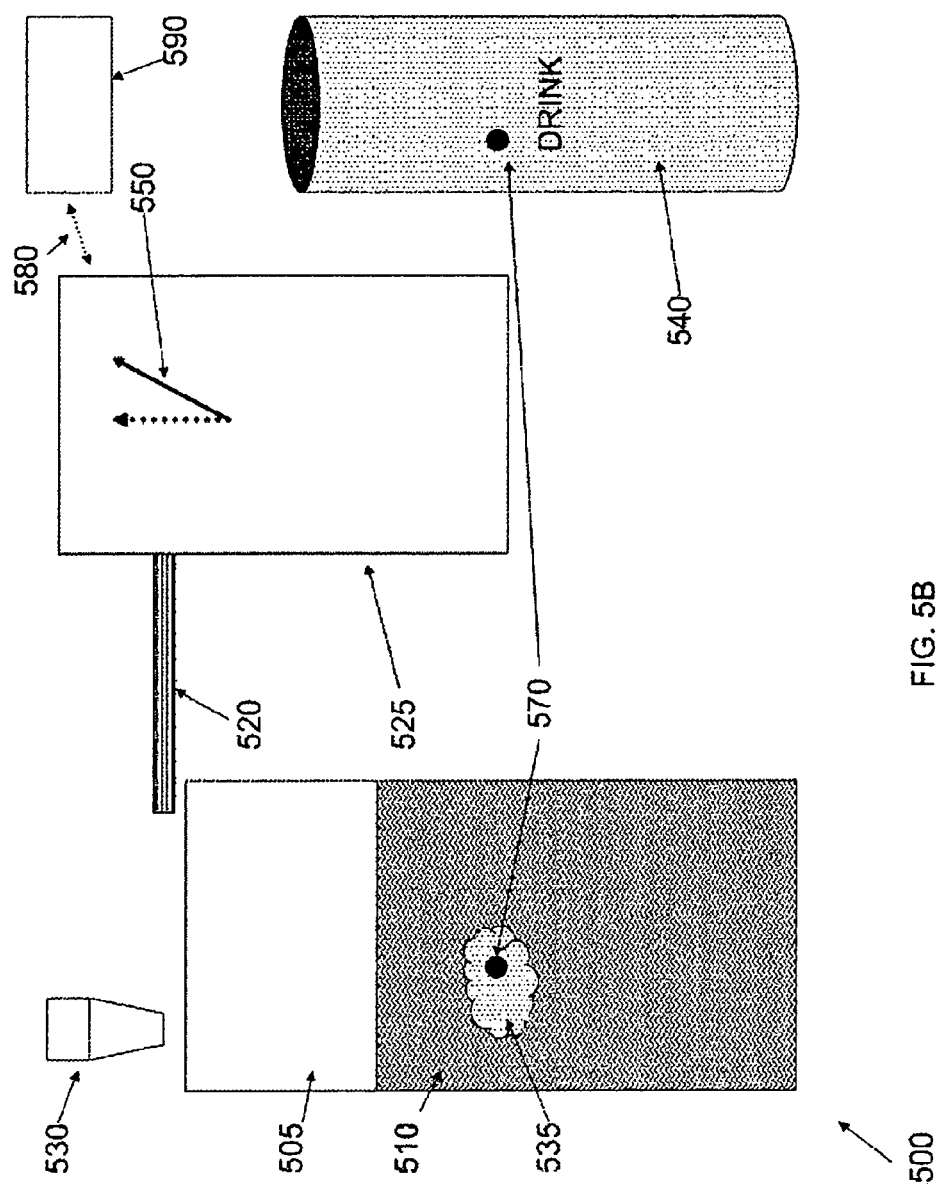
Figure 6:
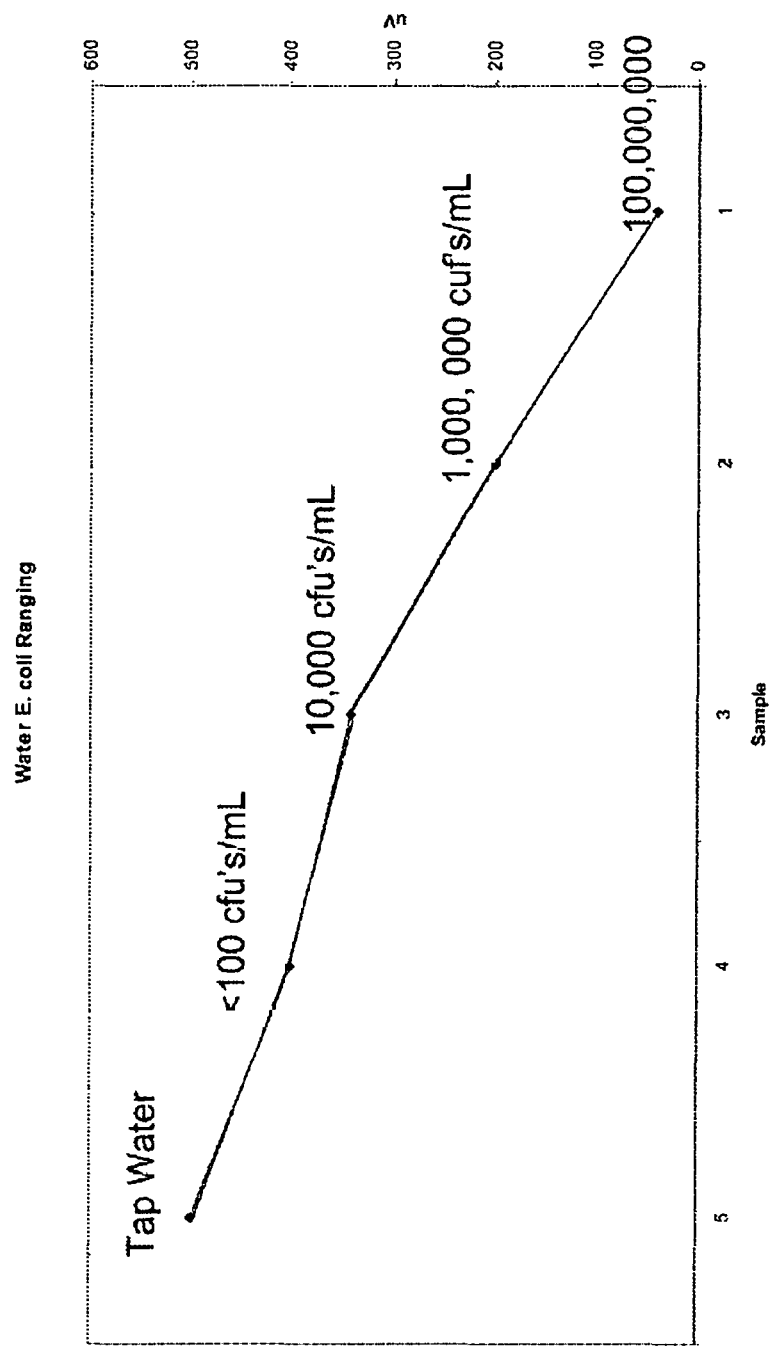
FIG. 6 shows a result associated with an Example of the instant invention.
Figure 7:
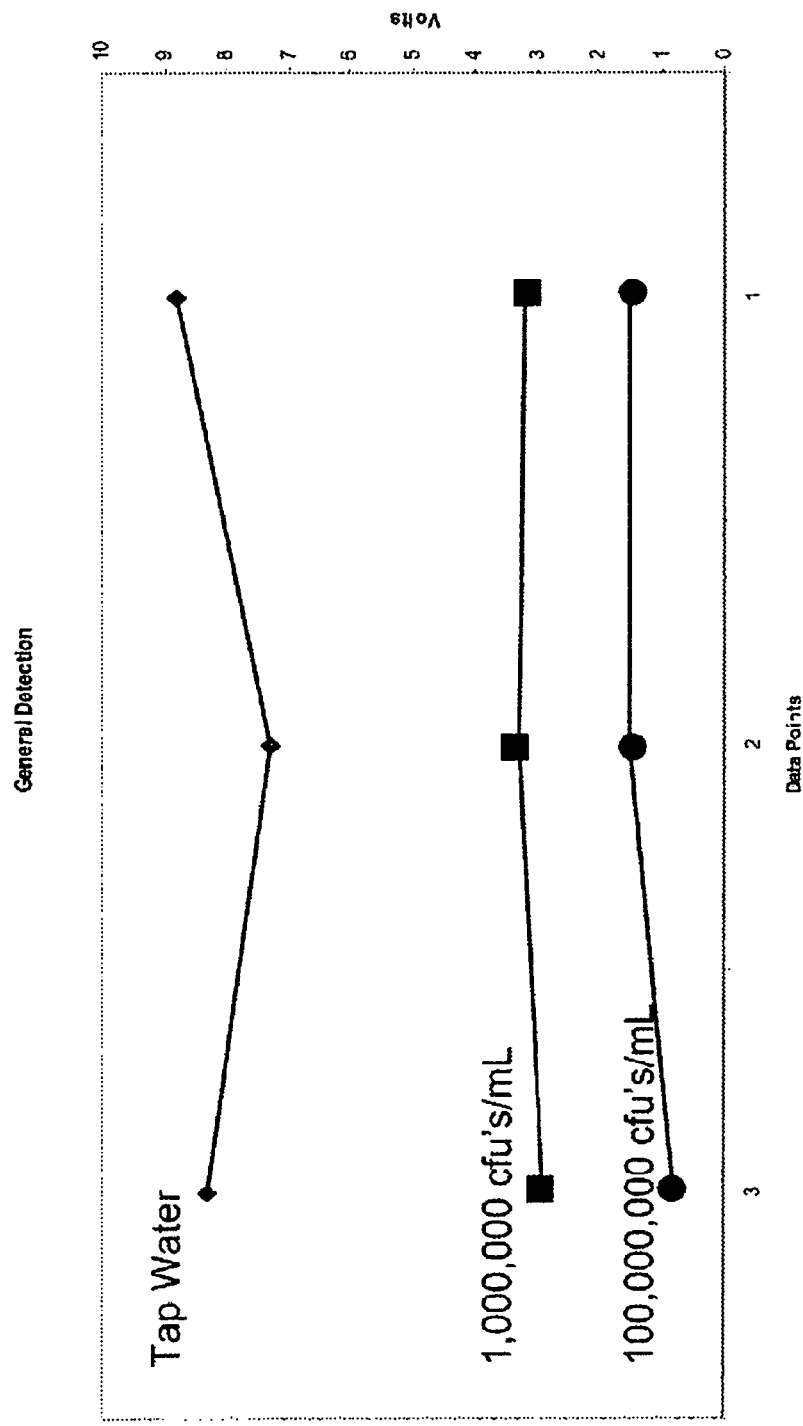
FIG. 7 shows results associated with said Example.
Figure 8:
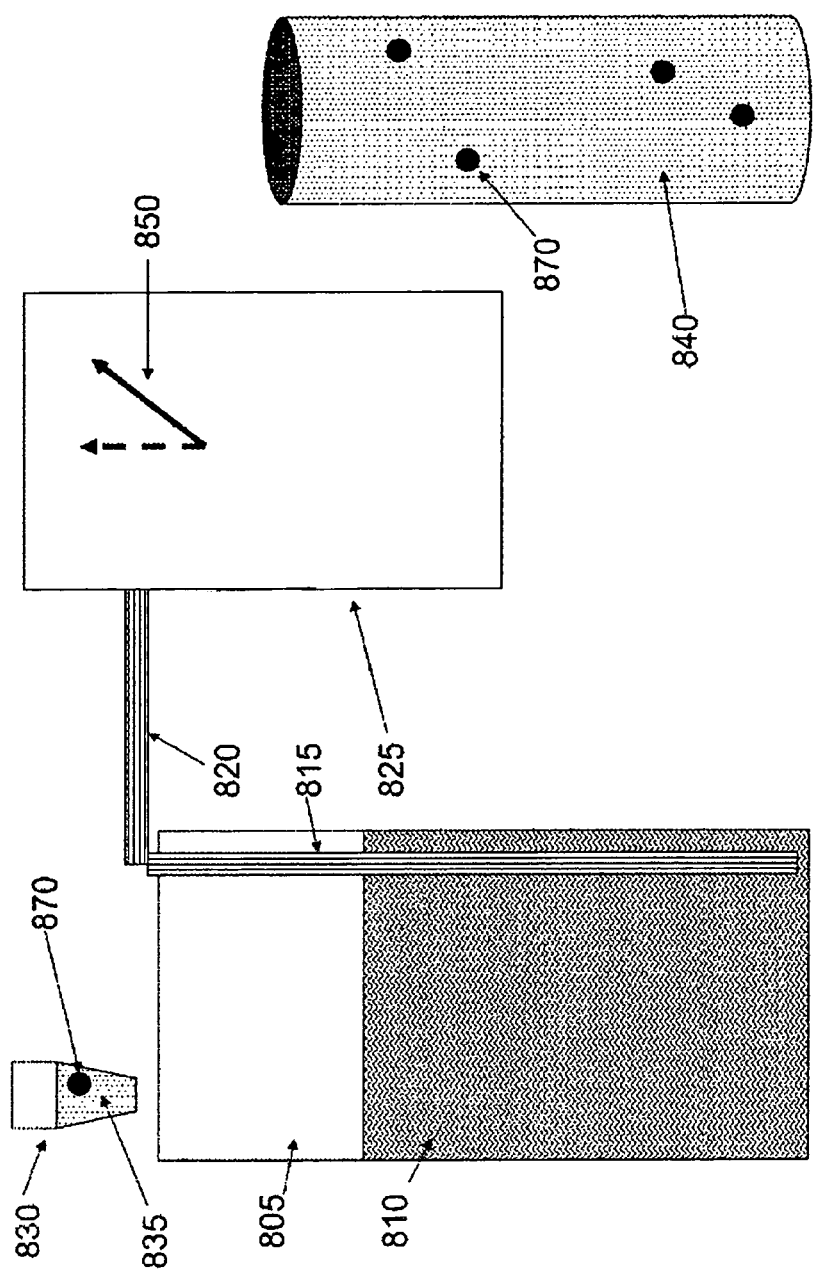
FIG. 8 shows a schematic embodiment of the instant invention, one in which sample injection is not required.

Attention is turned to FIG. 5B which shows that the portion 535 formerly in the liquid delivery element 530 has been injected into solution 510 where target 570 is now present. Changes in electrostatic fields in the solution 510 are identified by the single electrode 520 connected to the metering device 525. In general, clean sample 540, that is lacking bacteria or other predetermined residue or target 570, gives a relatively high electrical reading 550 in say AC or DC voltage in the metering device 525. Presence of bacteria or other targets 570 tends to cause output readings in the metering device to decrease. To note, there is only one electrode in use in the instant embodiment of the present invention. There is no need for a counter electrode, second electrode, introduction of voltage or current into the system from an exogenous source or the like. It is also understood that the metering device 525 may be a component of a detection unit [not shown] and may have a plurality of functions including but not limited to measuring a change in an electric signal, display said change, providing an alert. The metering device 525 may be electrically isolated in a Rutherford Cage or the like, though such arrangements are not shown in the instant embodiment. The metering device 525 may be associated with and/or controlled by a computing device, including but not limited to smartphones, tablet computers and mobile computing devices. The metering device 525 may also be in electrical connection 580 with a mobile computing device 590 that may be realized as a smartphone, tablet computer, laptop computer or the like. The mobile computing device 590 may include software and/or applications for allowing reading of outputs and results from the metering device 525.

Sixth Embodiment

Figure 9:
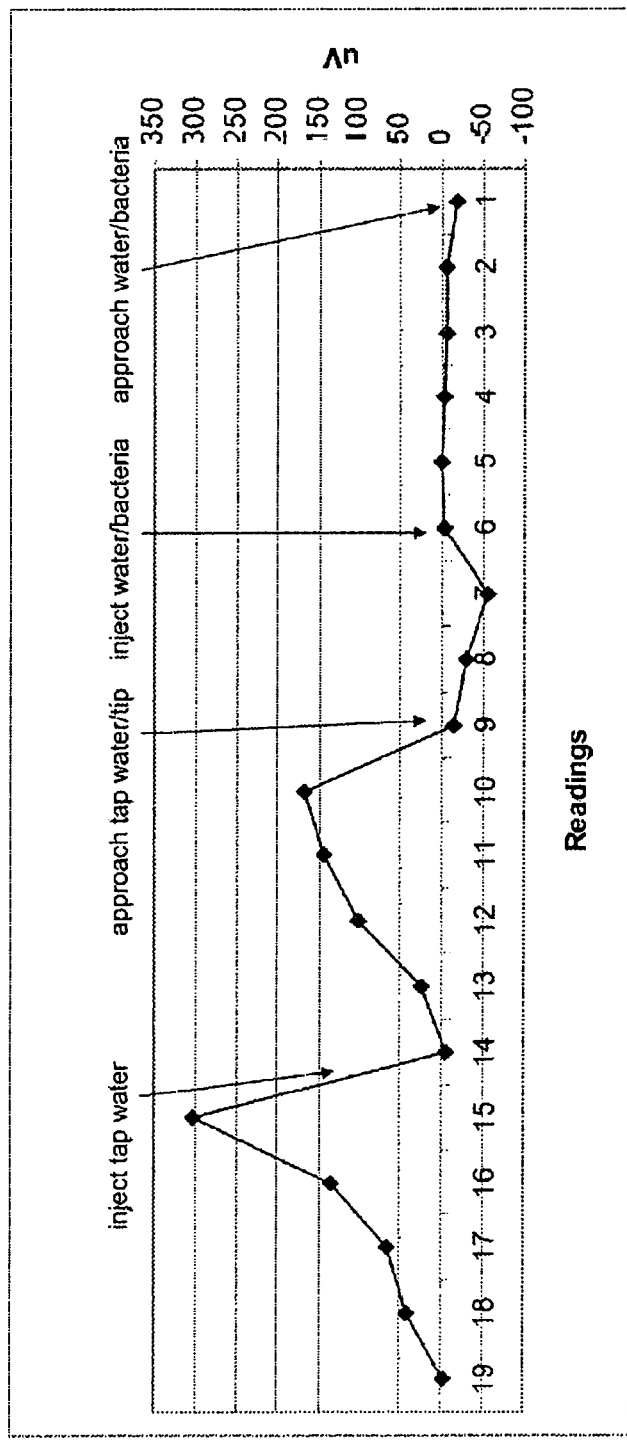
FIG. 9 shows results for experiments performed with an embodiment associated with FIG. 8.

The invention includes a method for determining the presence of a biological residue in a liquid sample, including the following: providing a sample; providing a container adapted to hold a liquid material; placing a conductive element in a portion of the container; adding an aqueous solution to a predetermined volume within the container, wherein a portion of the conductive element is in physical contact with the aqueous solution; attaching a dry region of the conductive element to an electrical metering device, wherein the contact involves a single electrical connection between the conductive element and a single terminal of the device; approaching the container with a liquid delivery element containing of a portion of the liquid sample; allowing readings in the electrical metering device to approach a zero value; injecting a portion of the liquid sample into the aqueous solution; measuring a change in an electrical parameter with the electrical metering device; and, determining the presence of the biological residue in the liquid sample as a function of a value of the change in the electrical parameter. It has been noted in experiments that bringing a pipette tip or the like close to the container with conductive element may lead to premature spurious signal in the metering device. Waiting a few seconds, 3-5 generally, allows the metering device to return to a zero or near zero value. At that time, the portion of the liquid sample may be injected; after injection, readings in the metering device may be either positive or negative. High positive signals, for example in DC voltage, +1000 microvolts, generally is associated with very clean liquid sample, lacking residue. Lower values, extending to negative values, suggest the presence of target residue. FIG. 9 described below shows an effect of bringing a pipette tip close to container, with concomitant generation of a single—independent of sample injection into container.

Seventh Embodiment

The invention also includes a method for determining the presence of a biological residue in a liquid sample, including the following: providing a sample; providing a container adapted to hold a liquid material; placing a conductive element in a portion of the container; attaching a region of the conductive element to an electrical metering device, wherein the contact involves a single electrical connection between the conductive element and a single terminal of the device; approaching the container with a liquid delivery element containing of a portion of the liquid sample; allowing readings in the electrical metering device to approach a zero value; injecting a portion of the liquid sample into the container; measuring a change in an electrical parameter with the electrical metering device; and, determining the presence of the biological residue in the liquid sample as a function of a value of the change in the electrical parameter. In this embodiment there is no requirement for liquid in the container. The container may be made of plastic, polymer, glass, quartz or any relevant material. Alternatively, there may be no container and one may spray the liquid portion of the sample directly in the conductive element.

Example 1

Aluminum foil [Reynolds] was used as supplied. A 1.5 milliliter centrifuge tube [Tamar, Israel] was charged with 1 milliliter of Jerusalem tap water. A piece of foil, 0.5 cm×5 cm was placed in the tap water so that part of the foil was wet and part was dry. To the dry portion was connected a crocodile clip; the other end of the clip was attached to a metal electrode sitting in the "voltage/resistance/temperature" position of a Fluke 189 multimeter [furthest right hole]. The meter was set to DC millivolts and allowed to approach a zero reading. 100 microliter Eppendorf pipettes with disposable polyethylene tips were employed to transfer 30 microliters of Jerusalem tap water alone or with varying concentrations of *E. coli* O157:H7. Injection of water sample without or with bacteria caused a change in the millivoltage reading in the Fluke metering device. The changes, both positive and negative, immediately after injection—for up to 3 seconds—were manually recorded. FIG. 6 shows results for the instant Example. Clean Jerusalem tap water, according to plating on agar plates, shows less than 10 cfu's per milliliter of bacterial contamination. Tap water gave the highest signals at around 500 micro-volts, with signal decreasing according an increase in bacteria present as labeled in the figure. FIG. 7 shows a consistency in output values as a function of bacterial levels present in the original sample solutions. Labeled reading values are in volts, wherein the highest readings are again associated with the cleanest samples, 9 volts being its output. It is understood that the instant Example could be performed with any aqueous solution including but not limited to water, soft drinks, hard liquor, pharmaceutical fluids, biological fluids, and laboratory samples. To note, only addition of sample causes a change in signal as shown in the graphs of FIG. 6 and FIG. 7. Measurement of AC or DC potential or some other electrical parameter on the solution in the centrifuge tube does not yield any discrimination, even if target is present. Rather, injection of target with the pipette serves to trigger a change in potential as recorded in the Fluke meter. Thus, sample addition may be a key feature for generating a measurable signal.

Example 2

Attention is turned to FIG. 8 which shows an embodiment associated with the present Example. A pipette tip 830 includes a portion 835 of a sample 840. Bringing the tip 830 into non-contact proximity of 20 centimeters or less towards a conductive element 815 leads to a signal 850 in an electrical meter device 825 that is in electrical communication with the conductive element 815 through the agency of an electrode 820. In a clean Jerusalem tap water experiment, approach of the tip towards the conductive element leads to a signal 850 of 150 microvolts in the meter 825; addition of the sample to liquid in container 805 containing an aqueous solution 810 leads to a signal in excess of 300 microvolts read in the meter. In a parallel experiment, a pipette tip 830 placed in a sample of water with 5,000 cfu's/mL of bacteria and then approached towards the same conductive element 815 associated with the electrode 820 and meter 825 did not lead to any increase in signal, which remained near zero as recorded by the meter 825. Addition of sample with the bacteria 870 led to a small negative signal in microvolts as displayed by the meter 825. The results of the two experiments are summarized in FIG. 9. It would appear that one need not actually inject portion 835 [FIG. 8] of sample 840; proximity of tip to conductive element 815 or just electrode 820 is enough to elicit signal 850 in electric meter device 825. It is believed that bacteria in the polluted sample cover static charge on the plastic [polypropylene] tip 830; absence of bacteria allows static charge on tip 830 to remain and static charge causes induction of the conductive element 815, an effect that is recorded in the meter 825.

Eighth Embodiment

Attention is turned to FIG. 10A, which shows a schematic view of an embodiment of the instant invention. A liquid 1010 is flowing through a pipe 1090 in the direction 1091 as shown. A conductive element 1015 is in physical contact with said flowing liquid 1010 and is electrically attached to an electrical metering unit 1025 at a single terminal. Flowing liquid 1010 may cause electrical signals to be generated in the conductive element 1015, those signals being reading in the electrical metering unit 1025. The electrical metering unit 1025 may optionally send 1095 signal data to a computing device 1097 by wireless or wired means. The computing device 1097 may interpret and/or display the signal data to a user (not shown). The computing device 1097 may also include a controller element adapted to receive readings from the metering device 1025 and provide a signal via an appropriate interface 1098 to a user as to a presence or absence of said residue in said liquid sample Liquids 1010 for the instant embodiment may be aqueous, organic or otherwise. Water is a typical liquid 1010 though other fluids may be tested by the instant embodiment. The original liquid sample does not have to be flowing; the portion of the liquid sample 1010 tested is allowed to flow as described above. The instant embodiment may be used to test the quality of liquid 1010, wherein quality may generally refer to the absence or presence of predetermined contaminants in the liquid 1010, including but not limited to bacteria, viral particles, dirt, salts, organic residues, or predetermined chemical materials. For a given liquid 1010, output signal in the metering device 1025 is generally higher the less contaminated a liquid 1010 sample is. Readings in the metering device 1025 are in real-time and reading values in AC or DC volts, Hertz, electrical resistance or the like reflect the quality state and cleanliness of the liquid 1010 contacted to the conductive element 1015.

Attention is turned to FIG. 10B, which shows an additional view of the instant embodiment. In this view, conductive element 1015 may be close to or in physical contact with an outer side of the pipe 1090, without any direct contact with the liquid 1010 in the pipe 1090. Flowing 1091 liquid 1010 gives off fluctuating electrical fields which may induce electron flow in the conductive element 1015; these fluctuations may be facilely measured in the passive electrical metering device 1025 physically contacted to the conductive element at a single terminal on the metering device 1025. Data from the metering device 1025 may be sent 1095 wirelessly or otherwise to a computing device 1097, where the data may be interpreted and/or displayed to a user by the computing device 1097 or an associated controller element. The metering device 1025 and the computing device 1097 may alternatively be a single element. A typical computing device may be a smartphone, handheld computing device, computer watch, tablet computer, laptop computer or other device with a graphical user interface 1098. In this embodiment, there is no physical contact between liquid 1010 and conductive element 1015 when the latter monitors the quality of the former.

Figure 10C:
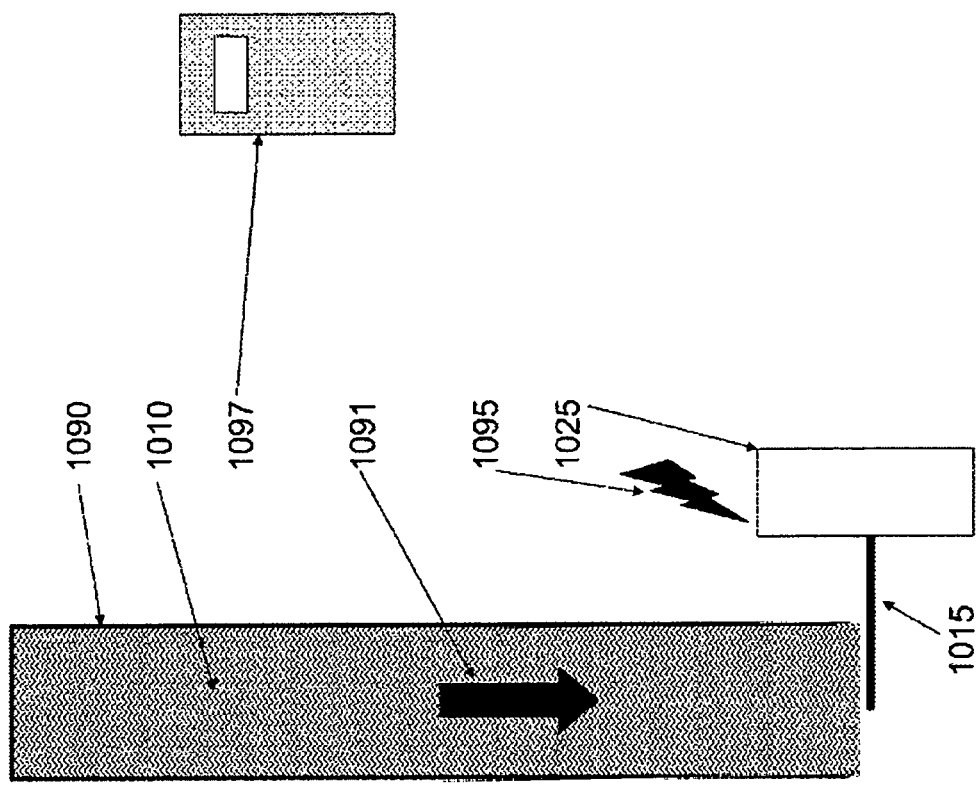
FIGS. 10A & 10B show schematic views of an embodiment of the instant invention.

Attention is turned to FIG. 10C which shows another physical arrangement of the instant embodiment. Liquid 1010 flowing 1091 in a pipe 1090 is directed towards a conductive element 1015, which is contacted by liquid 1010 when the latter leaves the pipe 1090. Liquid contact of conductive element 1015 leads to electrical phenomena recordable in an associated electrical metering device 1025, attached at a single position [there is no electrical circuit] to conductive element. It is understood that a pipe 1090 in the instant embodiment may be any element that may hold a liquid 1010 and allow said liquid 1010 to flow 1090 in a predetermined direction. Pipettes, hoses, pipes, syringes, sinks, toilets, showers, and the like are non-limiting examples of pipes 1090 according to the instant embodiment.

Figure 11A:
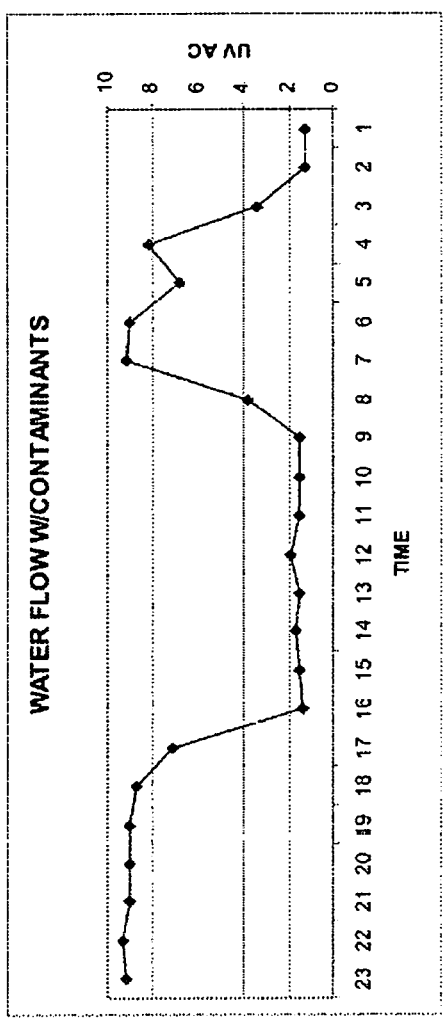
FIGS. 11A & 11B show data for experiments performed with an embodiment of the instant invention.

Attention is turned to FIG. 11A, which shows a result for use of the embodiment shown in FIG. 10C. In FIG. 11A, time is the X-axis, with each number, read from right to left, representing two seconds. Time points 2-8 show data for tap water flowing over an aluminum foil [Reynolds Diamond] attached at a single terminal to a recording Fluke 189 voltmeter. Values read are approximately 8 mV AC. Data points 9 to 16 show tap water contaminated with *E. coli* bacteria at a concentration of a few thousand cfu's per milliliter. Readings were quite depressed and were generally less than 2 mV AC. Data points 17 until the end of the graph again show tap water over the foil, and output readings for water lacking the bacteria again are between 8 and 10 mV AC. As shown, the outputs are in real time and presence of bacteria in flowing tap water is immediately identified by depressed AC voltage readings recorded by the Fluke multimeter. In actual water monitoring, such bacterial presence could lead to treatment or cessation of flow for said tap water.

Figure 11B:
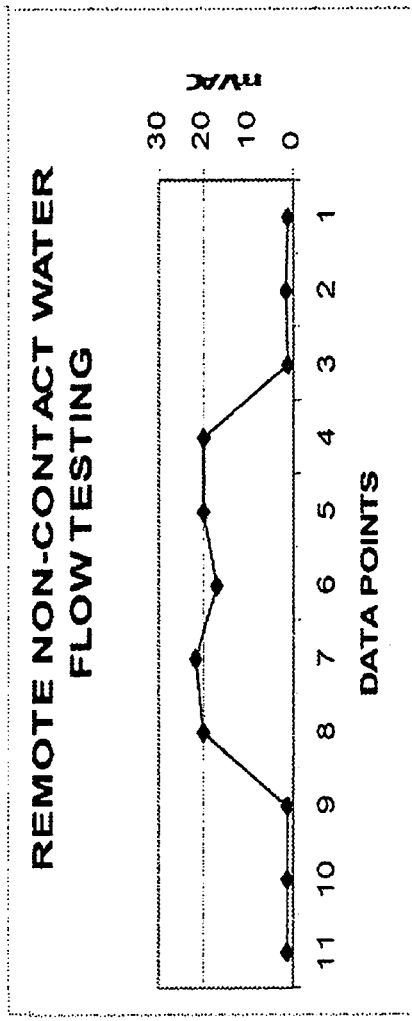

Attention is turned to FIG. 11B which shows output data for an embodiment similar to that shown in FIG. 10B. In FIG. 11B, data are again shown from right to left, with each point on the X axis representing two seconds of measurement in the Fluke meter set to AC millivolts. A piece of foil was lightly contacted to the outside of a PETE disposable cup, and tap water was allowed to flow towards a side of the cup opposite the foil. There was no contact between foil and water. Without water flowing, background values of less than 2 mV AC were recorded. Water flowing as shown in data points 4-8 led to output values of approximately 20 mV AC. Stopping water flow, as shown in data points 9 and forward led to a return to background values. The specific values when water was flowing depended greatly on the material used to separate between the aluminum foil conductive element and the flowing tap water. Certain plastics gave very high signals, whereas harder plastics often did not give any signal at all.

Figure 12A:
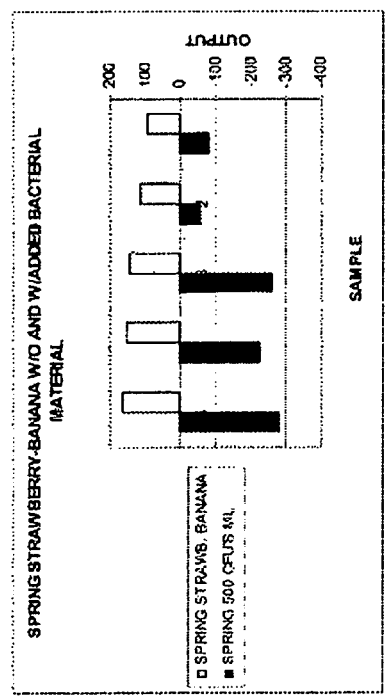
FIGS. 12A & 12B show data associated with experiments with alternative embodiments of the instant invention.

Attention is turned to FIG. 12A which shows output data for an embodiments similar to that shown in FIG. 10C. A commercially available fruit drink [Spring Banana-Strawberry, Rehovot, Israel] was used as is and with *E. coli* added to a concentration of 500 cfu's per milliliter. Samples of the drink were taken up in disposable 1000 uL pipette tips and directed towards a conductive element, generally aluminum foil. Samples lacking added bacteria showed positive signals generally 100 uV DC or higher; spiked samples showed negative signals, reaching as low as −250 uV DC. This system allows for facile quality control over commercial beverages by directing a flowing liquid at a static conductive element. One could obviously move the conductive element relative to a static fluid, though the output would be less consistent. Contaminated drink samples could be treated to stopped before bottling.

Figure 12B:
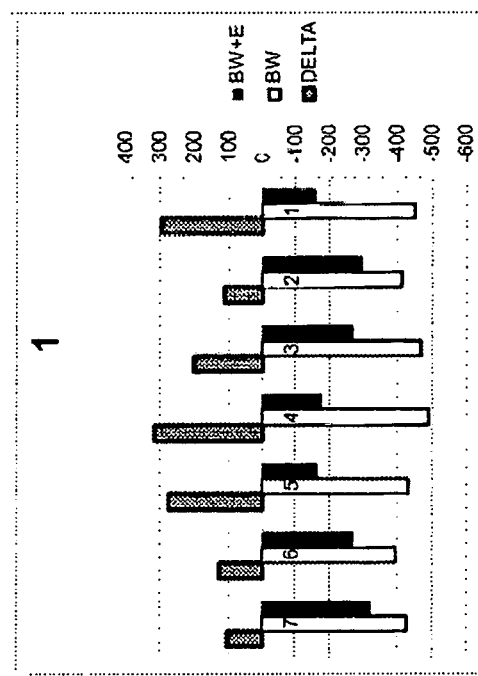

Attention is turned to FIG. 12B which shows an outcome of experiments run according to an embodiment of the instant invention. Water contacting 50,000 cfu's of general bacteria per milliliter and the same water with an additional 500 cfu's per milliliter of *E. faecalis* were testing by passing samples of the water past *E. faecalis* aluminum foil coated with antibodies specific for. Water harboring many bacteria but without the target bacterium showed very negative signals, generally below −400 uV DC. When *E. faecalis* was present at 1% of total bacterial population, signals were significantly lower, generally less negative than −300 uV DC. The delta values shown in grey show the difference between sample pairs—the system with the specific antibodies present on the conductive element allowed for detecting a specific target bacteria at 1% of total bacteria present in water samples.

Ninth Embodiment

Figure 13:
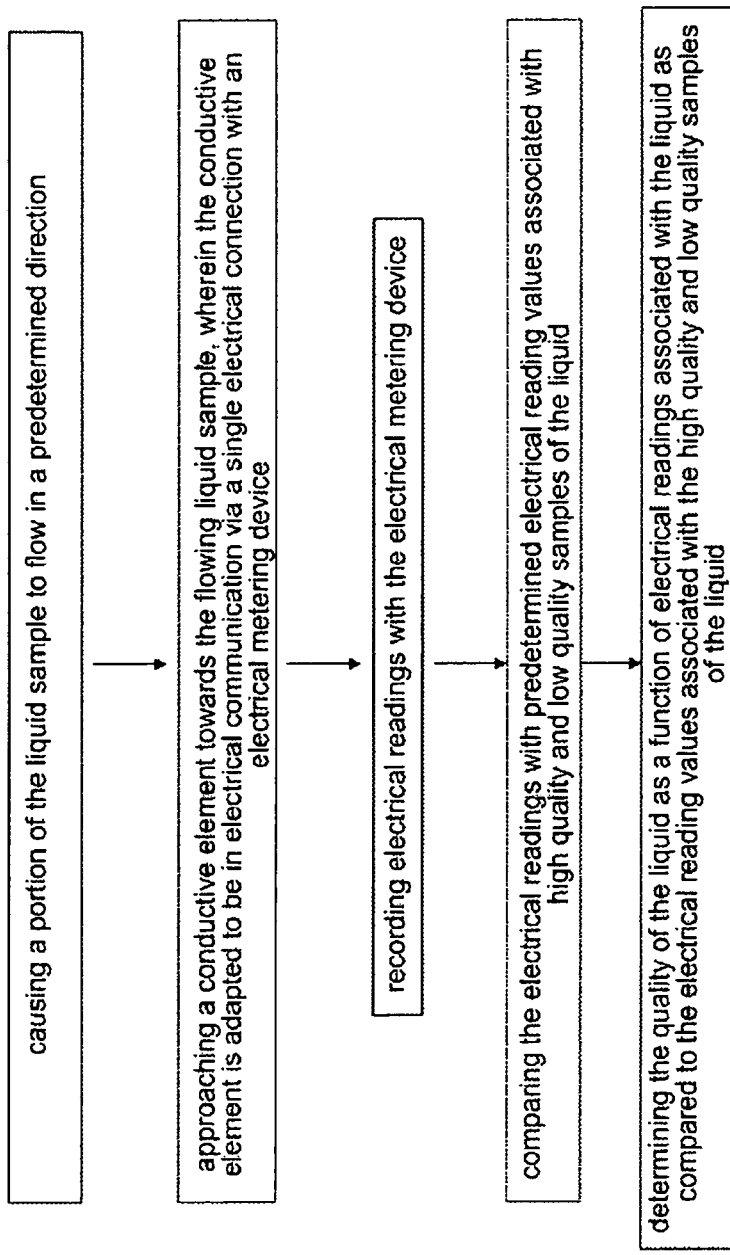
FIG. 13 shows a method associated with the instant invention.

Attention is turned to FIG. 13, which shows a method embodiment associated with the instant invention. The invention includes a method for determining the quality of a liquid sample, including the following: causing a portion of the liquid sample to flow in a predetermined direction; approaching a conductive element towards the flowing liquid sample, wherein the conductive element is adapted to be in electrical communication via a single electrical connection with an electrical metering device; recording electrical readings with the electrical metering device; comparing said electrical readings with predetermined electrical reading values associated with high quality and low quality samples of said liquid; and, determining the quality of the liquid as a function of electrical readings associated with the liquid as compared to the electrical reading values associated with the high quality and low quality samples of the liquid.

The conductive element may be any conductive or semiconductive material. Metals, polymers, inorganic semiconductors are all non-limiting examples for use in the role of conductive element. A metering device may be any device or material that is adapted to register an electrical signal associated with conductive element being in proximity to a flowing liquid sample. Any liquid may be used in the instant embodiment, though water and other aqueous-based solutions are generally preferred. "Quality" with respect to the instant invention may refer to a state of the liquid as defined by a user's requirement. Quality may refer for example to the presence or absence of biological material, bacteria, viral particles, inorganic chemicals, organic chemicals, pH state, or other parameter determined by a user. Determination of "quality" of liquid is performed by comparing output readings from the electrical metering device with predetermined values associated with acceptable quality and unacceptable quality liquid samples. For a non-limiting example, if a locale allows for 1000 cfu's per milliliter of bacteria in drinking water, one may determine output values for high quality water that meets this criterion and low quality water that does not. High quality water having 1,000 or fewer cfu's per milliliter may have output values of 15 mV AC or higher, whereas samples having lower output values of say 5 or 10 mV AC are known to have bacterial levels in excess of the predetermined allowed cutoff. Quality thus may refer to a given parameter or plurality of parameters associated with a liquid and any potential contaminants or physical features of said liquid.

Tenth Embodiment

Figure 14A:
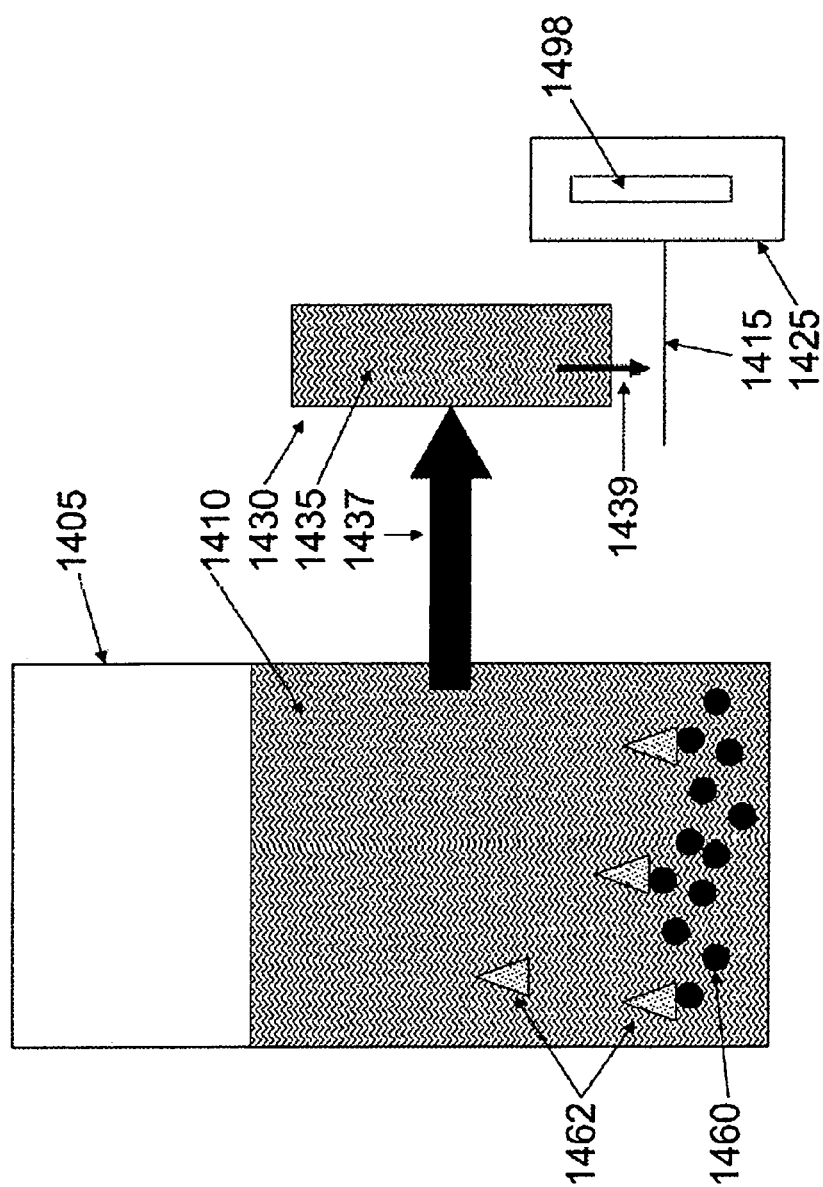
FIGS. 14A & 14B show schematic views of an embodiment of the instant invention associated with specific analyte detection.
Figure 14B:
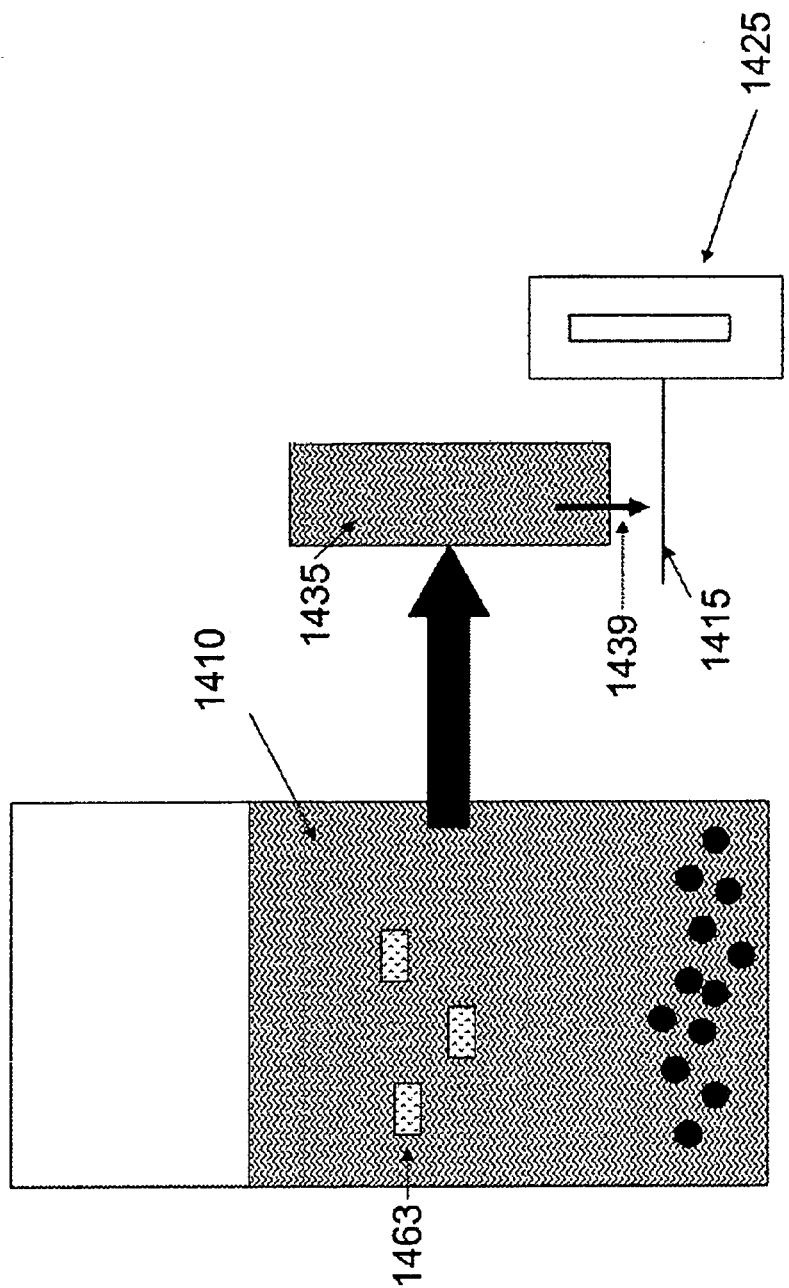

Attention is turned to FIG. 14A, which shows a schematic view of an embodiment of the instant invention. A container 1405 includes a liquid sample 1410 and antibodies 1460 may be free in liquid sample 1410 or may be associated with a solid element including but not limited to a portion of the container 1405. Target bacteria 1462 may bind to antibodies 1460 specific for said bacteria 1462. A portion 1435 of the liquid sample 1410 is transferred 1437 to a pipette 1430 or similar device and then allowed to flow 1439 over and contact a conductive element 1415 associated through a single electrical terminal to an electrical metering device 1425. Readings are recorded by the electrical metering device 1425 and may be displayed on an appropriate display 1498. Attention is turned to FIG. 14B, where a similar arrangement is shown, with a non-target bacteria 1463 present. The portion 1435 flowed 1439 onto the conductive element 1415 gives a different output in the electrical metering device 1425 due to the lack of bacteria 1463— antibody 1460 interactions (see FIG. 14A). Thus, by taking a portion 1435 of a supernatant of the liquid 1410, one may determine if a specific reaction between antibody 1460 and antigen or receptor and ligand or other materials has occurred in the liquid sample 1410 being interrogated.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the, method or structure may include additional ingredients, steps and/or parts, but only if the additional ingredients, steps and/or parts do not materially alter the basic and novel characteristics of the claimed composition, method or structure.

It is understood that the instant invention may be fully or partially integrated into a plurality of different devices including food safety or human diagnostic equipment. It is understood that embodiments of the instant invention could allow for measurement of many samples either sequentially or simultaneously, and the single experiments shown in the figures above is for convenience only. One obvious embodiment would be to use a compass or similar device, wherein the moving water or other liquid would cause a displacement of a metallic or magnetic element. The amount of displacement would be reflective of the state of the liquid and the presence or absence of any predetermined residues.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. The present invention could be employed for a wide variety of applications including but not limited to municipal water testing, beverage water testing, beverage testing, human diagnostics, food safety, homeland security and consumer testing of water and food products.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. It would be obvious for example that one could inject a sample into an empty container with or without a conductive element present in the container; one does not have to have a solution present in container to have a reading, though readings tend to be more consistent if one injects a sample into an aqueous solution in a portion of a container.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for determining the quality of a liquid sample, including the following:
   causing a portion of said liquid sample to flow in a predetermined direction in a liquid delivery element;
   positioning a conductive element such that it is not in direct contact with either said liquid sample or said liquid delivery element, wherein said conductive element is adapted to be in electrical communication via a single electrical connection with a passive electrical metering device;
   recording electrical readings with said electrical metering device;
   comparing said electrical readings with predetermined electrical reading values associated with high quality and low quality samples of said liquid; and,
   determining a quality of said liquid as a function of electrical readings associated with said liquid as compared to said electrical reading values associated with said high quality and low quality samples of said liquid.

2. The method according to claim 1, further comprising the step of:
   sensing an electrical field caused by said flow of at least a portion of said liquid sample.

3. The method according to claim 2, wherein said sensed electrical field is recorded as said electrical reading.

4. The method according to claim 1, wherein said recording is performed by a computing device.

5. The method according to claim 1, wherein said electrical reading is a function of a biological residue in said liquid sample.

6. The method according to claim 1, wherein said electrical reading is a function of a chemical residue in said liquid sample.

7. The method according to claim 1, wherein said electrical reading is a function of bacteria in said liquid sample.

8. The method according to claim 1, wherein said electrical reading is a function of pollution in said liquid sample.

9. The method according to claim 1, wherein said step of determining a quality of said liquid determines whether said liquid sample is drinkable.

* * * * *